US012636346B2

(12) United States Patent
Kim et al.

(10) Patent No.: US 12,636,346 B2
(45) Date of Patent: *May 26, 2026

(54) COMPOSITION FOR TREATING PAIN

(71) Applicant: KOLON LIFE SCIENCE, INC.,
Seoul (KR)

(72) Inventors: Sujeong Kim, Seoul (KR); Heonsik Choi, Seoul (KR); Kyoungbaek Choi, Seoul (KR); Minjung Kim, Seoul (KR); Hyeonyoul Lee, Ansan-si (KR); Minju Kim, Seoul (KR); Daewook Kim, Yongin-si (KR); Min Kim, Seoul (KR); Jangjoon Park, Seoul (KR); Kyung-Ran Kim, Yongin-si (KR); Hyelin Ji, Seoul (KR)

(73) Assignee: KOLON LIFE SCIENCE, INC.,
Seoul (KR)

( * ) Notice: Subject to any disclaimer, the term of this patent is extended or adjusted under 35 U.S.C. 154(b) by 972 days.

This patent is subject to a terminal disclaimer.

(21) Appl. No.: 17/876,293

(22) Filed: Jul. 28, 2022

(65) Prior Publication Data

US 2022/0362342 A1     Nov. 17, 2022

Related U.S. Application Data

(63) Continuation-in-part of application No. 15/754,849, filed as application No. PCT/KR2016/010480 on Sep. 20, 2016, now Pat. No. 11,433,145.

(30) Foreign Application Priority Data

Sep. 21, 2015     (KR) ........................ 10-2015-0133349

(51) Int. Cl.
*A61K 38/20*          (2006.01)
*C12N 15/86*          (2006.01)

(52) U.S. Cl.
CPC .......... *A61K 38/2066* (2013.01); *C12N 15/86* (2013.01)

(58) Field of Classification Search
CPC .............. A61K 38/2066; A61K 9/0019; A61K 48/005; C12N 15/86; C12N 2750/14143; C07K 14/5428; C12Y 401/01015
See application file for complete search history.

(56) References Cited

U.S. PATENT DOCUMENTS

| | | | | |
|---|---|---|---|---|
| 5,547,847 A | * | 8/1996 | Hagopian .......... | C07K 14/4713 436/811 |
| 7,544,669 B2 | | 6/2009 | Fontoura et al. | |
| 7,553,932 B1 | * | 6/2009 | Von Herrath ...... | C07K 16/2866 424/85.1 |
| 2008/0051357 A1 | * | 2/2008 | Chang ................ | A61K 31/7088 514/44 R |
| 2009/0010948 A1 | | 1/2009 | Huang et al. | |
| 2013/0115218 A1 | | 5/2013 | Reiter et al. | |
| 2013/0316404 A1 | * | 11/2013 | Roers ................ | C07K 14/5428 435/367 |

FOREIGN PATENT DOCUMENTS

| | | |
|---|---|---|
| EP | 1 621 208 A1 | 2/2006 |
| EP | 2 258 841 A1 | 12/2010 |
| KR | 10-2008-0007968 A | 1/2008 |
| WO | 2008/084115 A2 | 7/2008 |

OTHER PUBLICATIONS

Jean-Marc G Guedon et al., "Current gene therapy using viral vectors for chronic pain", Molecular Pain, 2015, pp. 1-23, vol. 11, No. 27.
D Wolfe et al., "A human trial of HSV-mediated gene transfer for the treatment of chronic pain", Gene Therapy, 2009, pp. 455-460, vol. 16.
Darren Wolfe, PhD, et al., "A Clinical Trial of Gene Therapy for Chronic Pain", Pain Medicine, 2009, pp. 1325-1330, vol. 10, No. 7.
International Search Report for PCT/KR2016/010480 dated Jan. 11, 2017.
Dénes B. et al., "Autoantigens Plus Interleukin-10 Suppress Diabetes Autoimmunity", Diabetes Technology & Therapeutics, Aug. 2010, vol. 12, No. 8, pp. 649-661 (19 pages).
Intellectual Property Office of Singapore, Communication dated Sep. 14, 2018, issued in corresponding Singaporean Application No. 11201800229U.
Denes, B. et al., 'Durable Multicomponent Vaccine Suppression of Diabetes Autoimmunity', Molecular Therapy. 2009, vol. 17, Supplement 1, p. S67, Abstract 170, 1 page.
Weiss, K. et al., 'Herpes simplex virus-based gene therapies for chronic pain', Journal of Pain and Palliative Care Pharmacotherapy. 2012, vol. 26, No. 3, pp. 291-293, 4 pages.
Srinivasan, R. et al., 'HSV vectors for gene therapy of chronic pain', Current Opinion in Molecular Therapeutics. 2008, vol. 10, No. 5, pp. 449-455, 7 pages.
Australian Patent Office; Communication dated Oct. 18, 2018 issued in corresponding Application No. 2016327213.
Erin D. Milligan et al., "Controlling pathological pain by adenovirally driven spinal production of the anti-inflammatory cytokine, interleukin-10", European Journal of Neuroscience, vol. 21, pp. 2136-2148, 2005, 13 pages total.

(Continued)

*Primary Examiner* — J. E. Angell
*Assistant Examiner* — Julio Washington Gomez Rodriguez
(74) *Attorney, Agent, or Firm* — Sughrue Mion, PLLC

(57)          ABSTRACT

A composition useful for alleviating or treating pain and uses thereof are disclosed. The composition containing glutamate decarboxylase and a gene coding for an anti-inflammatory cytokine. A method for alleviating or treating pain of a subject includes administering the composition to the subject.

13 Claims, 7 Drawing Sheets
Specification includes a Sequence Listing.

(56) References Cited

OTHER PUBLICATIONS

Jean-Philippe Vit et al., "Adenovector GAD65 gene delivery into the rat trigeminal ganglion produces orofacial analgesia", Molecular Pain, vol. 5, No. 1, Aug. 2009, 11 pages total.

Bela Denes et al., "Suppression of Hyperglycemia in NOD Mice After Inoculation With Recombinant Vaccinia Viruses", Molecular Biotechnology, vol. 34, No. 3, Nov. 2006, pp. 317-327, 11 pages total.

Sofie Robert et al., "Oral Delivery of Glutamic Acid Decarboxylase (GAD)-65 and IL10 by Lactococcus lactis Reverses Diabetes in Recent-Onset NOD Mice", Diabetes, vol. 63, Aug. 2014, pp. 2877-2887, 12 pages total.

European Patent Office; Communication dated Mar. 11, 2019 issued in counterpart European Application No. 16848886.4.

Milligan et al., "Repeated intrathecal injections of plasmid DNA encoding interleukin-10 produce prolonged reversal of neuropathic pain", Pain, 2006, vol. 126, pp. 294-308 (total 15 pages).

Kanao et al., "Gene Transfer of Glutamic Acid Decarboxylase 67 by Herpes Simplex Virus Vectors Suppresses Neuropathic Pain Induced by Human Immunodeficiency Virus gp120 Combined with ddC in Rats", Anesthesia & Analgesia, Jun. 2015, vol. 120, No. 6, pp. 1394-1404 (total 11 pages).

Liu et al., "Release of GABA from sensory neurons transduced with a GAD67-expressing vector occurs by non-vesicular mechanisms", Brain Research, 2005, pp. 297-304 (total 8 pages).

Kim et al., "AAV-GAS gene for rat models of neuropathic pain and Parkinson's disease", Acta Neurochirurgica, Supplement, vol. 101, 2008, pp. 99-105 (8 pages total).

Song et al., "Construction and identification of eukaryotic expression vector containing GAD65 fragment and IL-10 gene", Chin Med Biotechnol, 2007, vol. 2, No. 2, pp. 105-109 (5 pages total).

EAU-439 *Lactococcus lactis* subsp. cremoris Strain SAGX0037, downloaded 5/23/3030, pp. 1-8.

Shanks et al, Are animal models predictive for humans?, Philosophy, Ethics, and Humanities in Medicine 2009, pp. 1-20.

Wu et al, Gene Therapy for the Management of Pain, Anesthesiology 2001; 94:1119-32.

Huang et al, Development of Viral Vectors for Gene Therapy for Chronic Pain, Pain Research and Treatment, pp. 1-8.

Thakur et al, Viral vector mediated continuous expression of interleukin-10 in DRG alleviates pain in type 1 diabetic animals, Molecular and Cellular Neuroscience 72 (2016) 46-53.

Palfi et al, Efficacy of codelivery of dual AAV2/5 vectors in the murine retina and hippocampus, Hum Gene Then Aug. 2012;23(8): 847-58.

Hirai etal, Intrathecal AAV Serotype 9-mediated Delivery of shRNA Against TRPV1 Attenuates Thermal Hyperalgesia in a Mouse Model of Peripheral Nerve Injury, Molecular Therapy, 2014, pp. 409-419.

* cited by examiner

[Fig. 3]
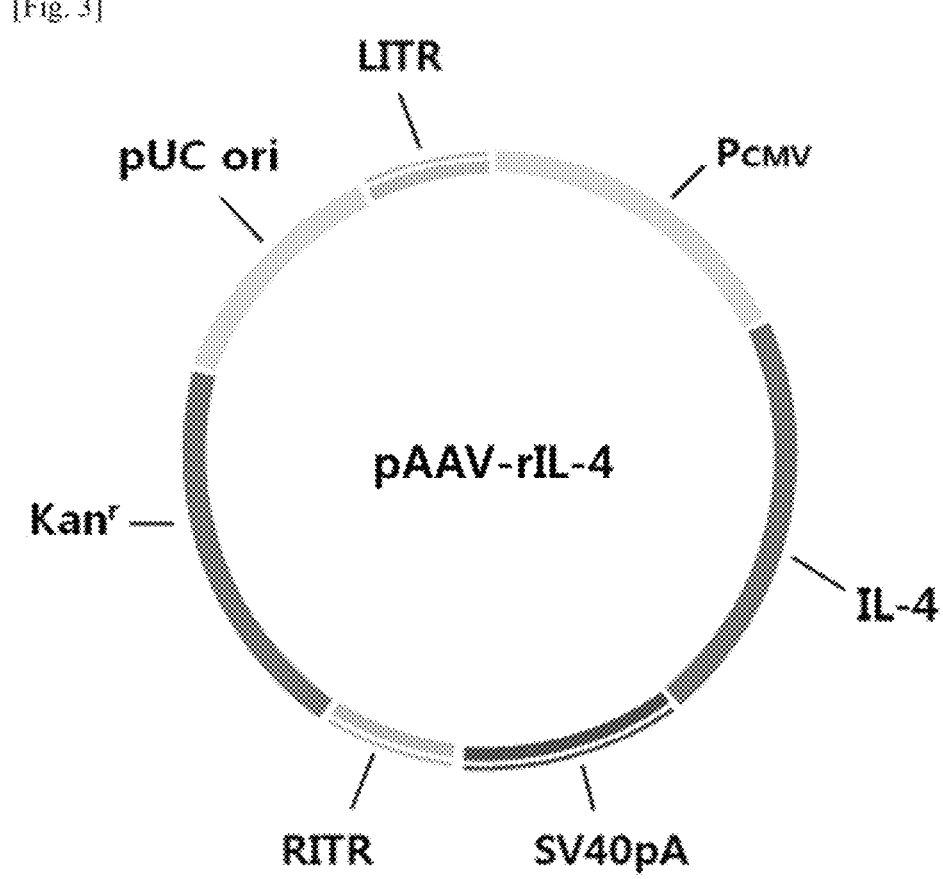

[Fig. 4]
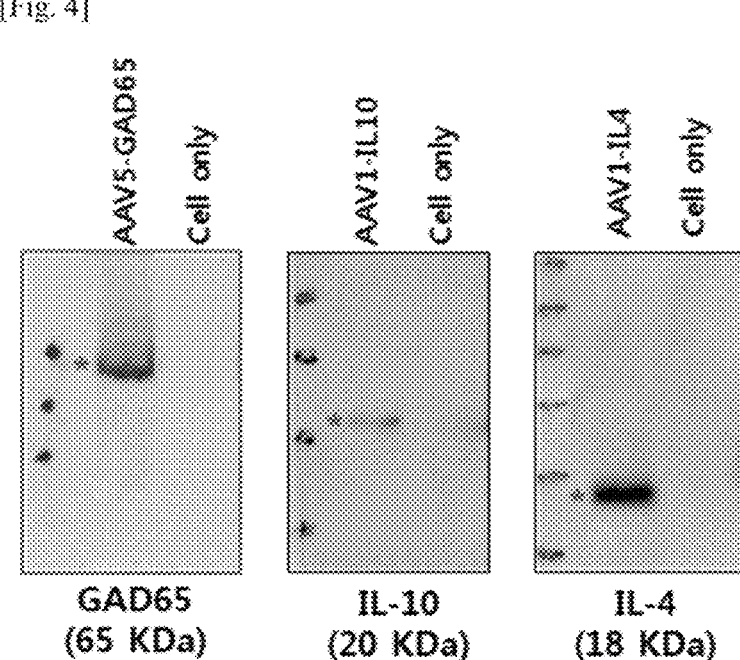
GAD65
(65 KDa)
IL-10
(20 KDa)
IL-4
(18 KDa)
[Fig. 5]
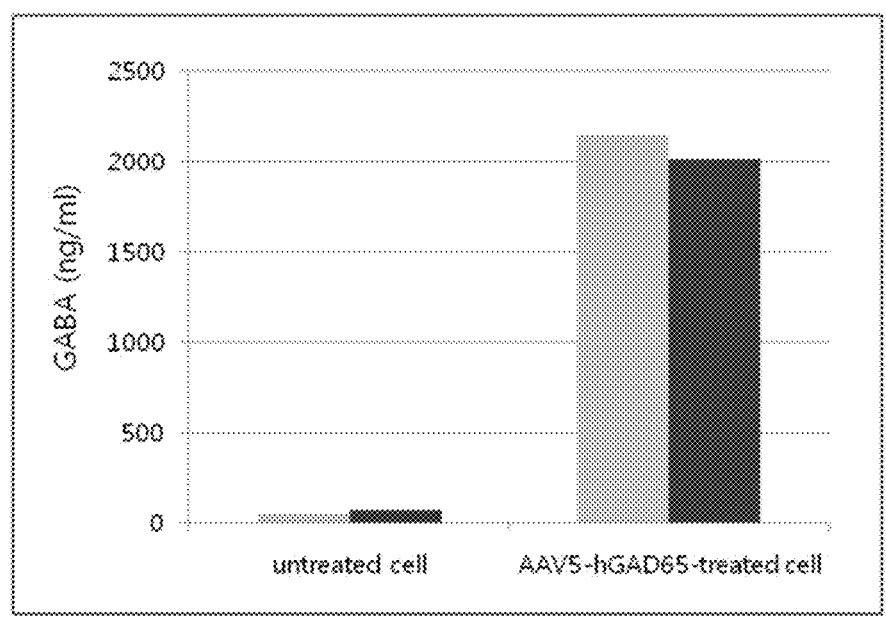

[Fig. 6]
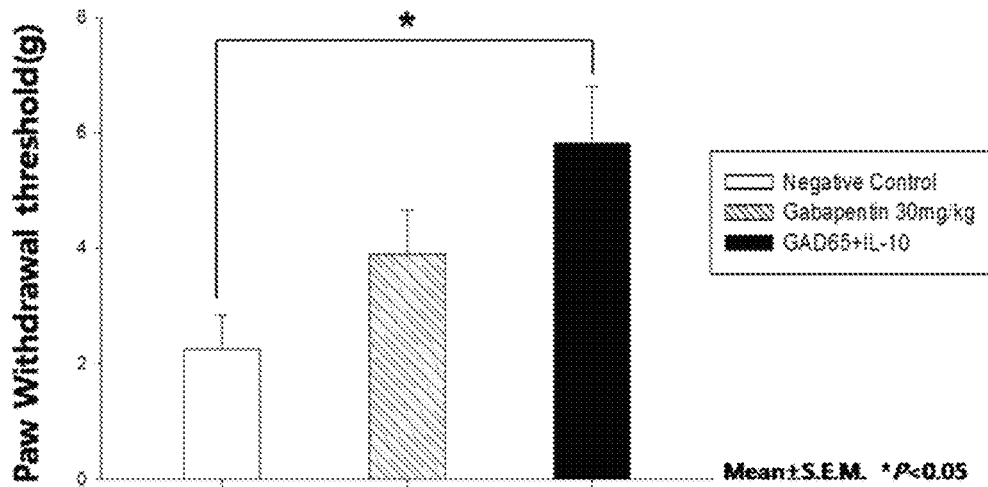
[Fig. 7]
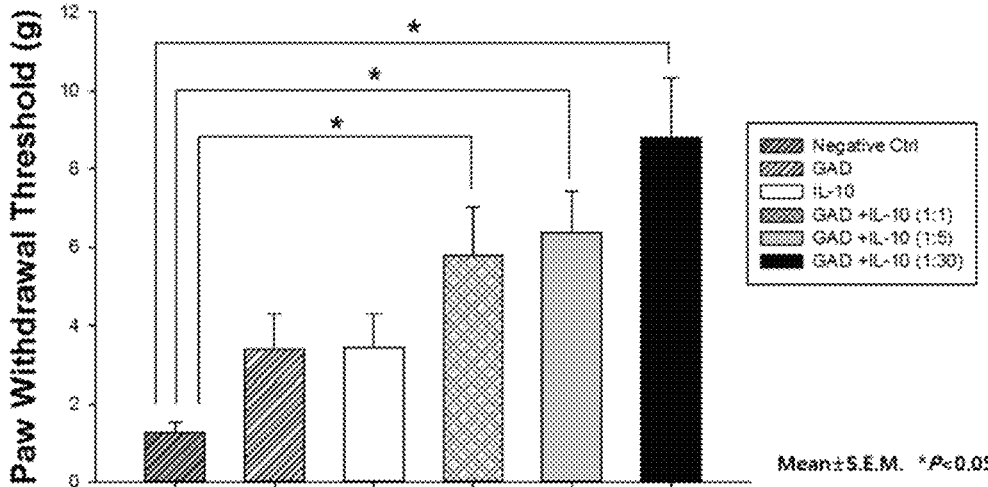

[Fig. 8]
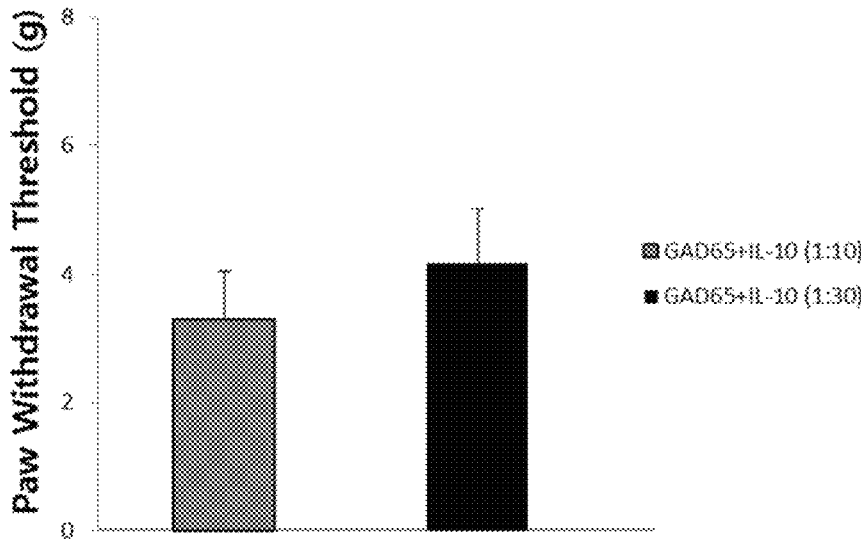
[Fig. 9]
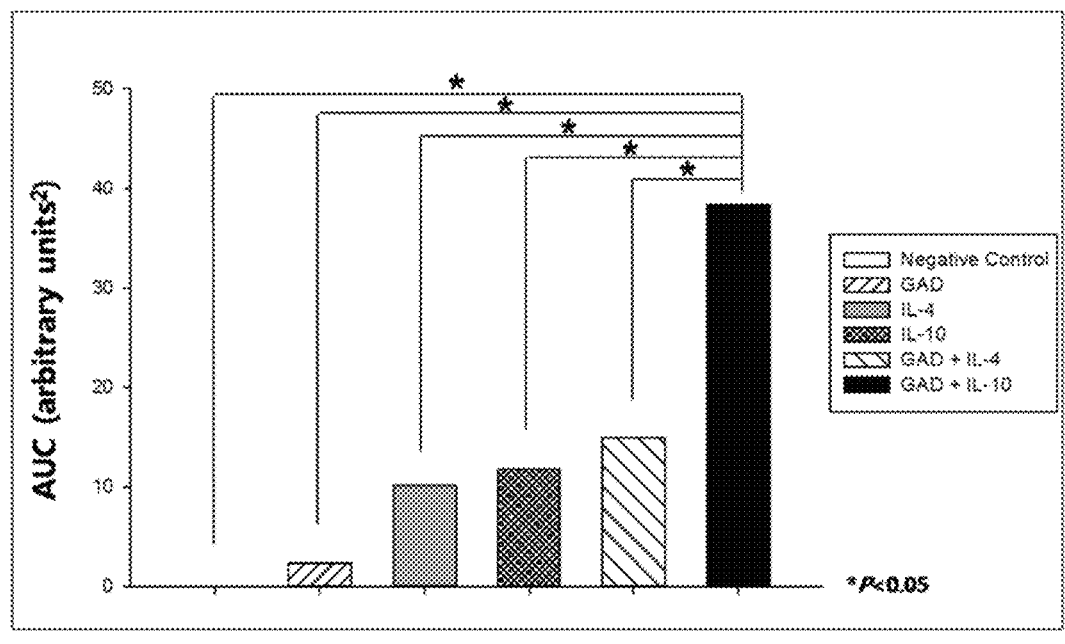

[Fig. 10]
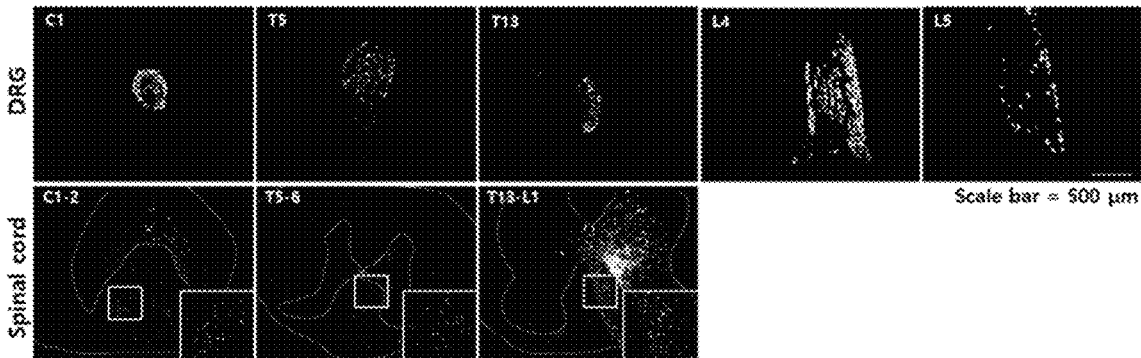

SEQUENCE LISTING

```
Sequence total quantity: 25
SEQ ID NO: 1              moltype = AA  length = 585
FEATURE                   Location/Qualifiers
source                    1..585
                          mol_type = protein
                          organism = Homo sapiens
SEQUENCE: 1
MASPGSGFWS FGSEDGSGDS ENPGTARAWC QVAQKFTGGI GNKLCALLYG DAEKPAESGG  60
SQPPRAAARK AACACDQKPC SCSKVDVNYA FLHATDLLPA CDGERPTLAF LQDVMNILLQ  120
YVVKSFDRST KVIDFHYPNE LLQEYNWELA DQPQNLEEIL MHCQTTLKYA IKTGHPRYFN  180
QLSTGLDMVG LAADWLTSTA NTNMFTYEIA PVFVLLEYVT LKKMREIIGW PGGSGDGIFS  240
PGGAISNMYA MMIARFKMFP EVKEKGMAAL PRLIAFTSEH SHFSLKKGAA ALGIGTDSVI  300
LIKCDERGKM IPSDLERRIL EAKQKGFVPF LVSATAGTTV YGAFDPLLAV ADICKKYKIW  360
MHVDAAWGGG LLMSRKHKWK LSGVERANSV TWNPHKMMGV PLQCSALLVR EEGLMQNCNQ  420
MHASYLFQQD KHYDLSYDTG DKALQCGRHV DVFKLWLMWR AKGTTGFEAH VDKCLELAEY  480
LYNIIKNREG YEMVFDGKPQ HTNVCFWYIP PSLRTLEDNE ERMSRLSKVA PVIKARMMEY  540
GTTMVSYQPL GDKVNFFRMV ISNPAATHQD IDFLIEEIER LGQDL                  585

SEQ ID NO: 2              moltype = DNA  length = 2824
FEATURE                   Location/Qualifiers
source                    1..2824
                          mol_type = genomic DNA
                          organism = Homo sapiens
SEQUENCE: 2
gcggccgccc gcacttcccg cctctggctc gcccgaggac gcgctggcac gcctcccacc  60
ccctcactct gactccagct ggcgtgcatg gtctgcctcg catcctcacg actcagctcc  120
ctccctctct cgtgtttttt tcctccgccg ccccctcatt catcccact gggctccctt  180
```

-continued

```
tccctcaaat gctctggggc tctccgcgct ttcctgagtc cgggctccga ggacccttag  240
gtagtcccgg tctcttttaa agctccccgg cttccaaagg gttgccacgt ccctaaaccc  300
tgtctccagc tcgcatacac acacgcacag acacgcacgt tttctgttcc tgcgtgacac  360
ccgccctcgc cgctcggccc cgccggtccc cgcgcggtgc cctcctcccg ccacacgggc  420
acgcacgcgc gcgcagggcc aagcccgagg cagctcggca ctcgcaggcg  480
acctgctcca gtctccaaag ccgatggcat ctccgggctc tggctttttgg tctttcgggt  540
cggaagatgg ctctggggat tccgagaatc ccggcacagc gcgagcctgg tgccaagtgg  600
ctcagaagtt cacgggcggc atcggaaaca aactgtgcgc cctgctctac ggagacgccg  660
agaagccggc ggagagcggc gggagccaac ccccgcgggc cgccgcccgg aaggccgcct  720
gcgcctgcga ccagaagccc tgcagctgct ccaaagtgga tgtcaactac gcgtttctcc  780
atgcaacaga cctgctgccg gcgtgtgatg gagaaaggcc cactttggcg tttctgcaag  840
atgttatgaa cattttactt cagtatgtgg tgaaaagttt cgatagatca accaaagtga  900
ttgatttcca ttatcctaat gagcttctcc aagaatataa ttgggaattg gcagaccaac  960
cacaaaattt ggaggaaatt ttgatgcatt gccaaacaac tctaaaatat gcaattaaaa  1020
cagggcatcc tagatacttc aatcaacttt ctactggttt ggatatggtt ggattagcag  1080
cagactggct gacatcaaca gcaaatacta acatgttcac ctatgaaatt gctccagtat  1140
ttgtgctttt ggaatatgtc acactaaaga aaatgagaga aatcattggc tggccagggg  1200
gctctggcga tgggatattt tctcccggtg gcgccatatc taacatgtat gccatgatga  1260
tcgcacgctt taagatgttc ccagaagtca aggagaaagg aatggctgct cttcccaggc  1320
tcattgcctt cacgtctgaa catagtcatt tttctctcaa gaagggagct gcagccttag  1380
ggattggaac agacagcgtg attctgatta aatgtgatga gagagggaaa atgattccat  1440
ctgatcttga aagaaggatt cttgaagcca aacagaaagg gtttgttcct ttcctcgtga  1500
gtgccacagc tggaaccacc gtgtacgag catttgaccc cctcttagct gtcgctgaca  1560
tttgcaaaaa gtataagatc tggatgcatg tggatgcagc ttggggtggg ggattactga  1620
tgtcccgaaa acacaagtgg aaactgagtg gcgtggagag ggccaactct gtgacgtgga  1680
atccacacaa gatgatggga gtcccttttgc agtgctctgc tctcctggtt aggaagagag  1740
gattgatgca gaattgcaac caaatgcatg cctcctacct ctttcagcaa gataaacatt  1800
atgacctgtc ctatgacact ggagacaagg ccttacagtg cggacgccac gttgatgttt  1860
ttaaactatg gctgatgtgg agggcaaagg ggactaccgg gtttgaagcg catgttgata  1920
aatgtttgga gttggcagag tatttataca acatcataaa aaaccgagaa ggatatgaga  1980
tggtgtttga tgggaagcct cagcacacaa atgtctgctt ctggtacatt cctccaagct  2040
tgcgtactct ggaagacaat gaagagagaa tgagtcgcct ctcgaaggtg gctccagtga  2100
ttaaagccag aatgatggag tatggaacca caatggtcag ctaccaaccc ttgggagaca  2160
aggtcaattt cttccgcatg gtcatctcaa acccagcggc aactcaccaa gacattgact  2220
tcctgattga agaaatagaa cgccttggac aagatttata ataaccttgc tcaccaagct  2280
gttccacttc tctagagaac atgccctcag ctaagccccc tactgagaaa cttcctttga  2340
gaattgtgcg acttcacaaa atgcaaggtg aacaccactt tgtctctgag aacagacgtt  2400
accaattatg gagtgtcacc agctgccaaa atcgtaggtc ttggctctgc tggtcactgg  2460
agtagttgct actcttcaga atatggacaa agaaggcaca ggtgtaaata tagtagcagg  2520
atgaggaacc tcaaactggg tatcattttg cacgtgctct tctgttctca aatgctaaat  2580
gcaaacactg tgtatttatt agttaggtgt gccaaactac cgttcccaaa ttggtgtttc  2640
tgaatgacat caacattccc ccaacattac tccattacta aagacagaaa aaaataaaaa  2700
cataaaatat acaaacatgt ggcaacctgt tcttcctacc aaatataaac ttgtgtatga  2760
tccaagtatt ttatctgtgt tgtctctcta aacccaaata aatgtgtaaa tgtggacaca  2820
tctc                                                                2824
```

```
SEQ ID NO: 3          moltype = DNA   length = 1758
FEATURE               Location/Qualifiers
misc_feature          1..1758
                      note = Optimized human GAD65
source                1..1758
                      mol_type = other DNA
                      organism = synthetic construct
SEQUENCE: 3
atggcatctc cgggctccgg cttttggtcc ttcgggtcgg aagatggctc aggggattcc  60
gagaatcccg gcacagcgcg ggcctggtgt caagtggctc agaagttcac gggcggcatc  120
ggaaacaaac tgtgtgccct gctctacggc gacgccgaga gcccgcaga gagcggcggg  180
agccaacccc gcgggccgc cgcccggaag gccgcctgcg cctgtgacca gaagccctgc  240
tcatgcagca aggtagatgt caactacgcg tttctccatg ccacagatct gctgccggct  300
tgcgacggtg aaaggcccac tttggccttt ctgcaggatg ttatgaacat tctgctgcag  360
tacgtggtga aaagtttcga ccggtcaacc aaagtgatcg actttcacta tcctaatgaa  420
cttctccagg agtacaattg ggagctggct gaccagccac agaacctgga ggaaatcttg  480
atgcattgcc aaactactct aaaatatgca attaaaacag gccatcctag atacttcaac  540
cagctttcta ccggtttgga tatggtgggg ctggcagcga atccaccgca  600
aataccaaca tgttcaccta tgagatcgct cctgtcttcg tgcttttgga atacgtcacc  660
ctaaagaaga tgcgtgaaat cattggctgg ccaggaggct ctggtgatgg tatattttct  720
cccgcggcgc cgatctctaa catgtatgcc atgatgatcg cacgctttaa gatgttccca  780
gaagtcaagg agaaaggaat ggctgctctt cccaggctca ttgccttcac gagtgaacac  840
agtcactttt ccctcaagaa ggggctgcc gcttagggca tcggaacaga cagcgtgagat  900
ctgataaagt gcgacgagag agggaaaatg attccatctg atcttgagag aaggattctt  960
gaagccaaac agaaagggtt tgtcctttc tcgtgagtg ccacagctgg aaccaccgtg  1020
tacgcgcat ttgaccccct cttagctgtc gcggatatat gtaagaagta taagatctgg  1080
atgcacgtgg atgctgcttg gggtggggga ttactgatgt ccaggaaaca caagtggaaa  1140
ctgtctggcg tggagcgcgc caacaacgtg acgtggaatc cacacaaaat gatggagtc  1200
cctttgcagt gctctgctct cctggttcga aagagggac tgatgcagaa ttgcaaccaa  1260
atgcatgcct cctacctctt tcagcaggat aaacattatg acctgtctta cgacactggt  1320
gacaggccc tgcagtgtgg cgccacgtt gatgtattca agctatggct gatgtggagg  1380
gcaagggga ctaccggttt tgaagcccat gttgacaaat gtctggagtt ggcagagtat  1440
ttatacaata tcataaaaaaa ccgagaagga tatgagatgg tgtttgatgg caagcctcag  1500
```

-continued

```
cacacaaatg tctgcttctg gtacatccct cccagcctac gtactctgga ggacaacgaa    1560
gagagaatga gtcgcctctc gaaggtggct ccagtgatta aagccagaat gatggagtat    1620
ggaaccacaa tggtcagcta ccaacccttg ggggacaagg taaatttctt ccgcatggtc    1680
atctcaaacc cagcggcaac tcaccaagac attgatttcc tgattgaaga gatcgagcgg    1740
ctcggccagg atctgtga                                                  1758

SEQ ID NO: 4              moltype = AA   length = 594
FEATURE                   Location/Qualifiers
source                    1..594
                          mol_type = protein
                          organism = Homo sapiens
SEQUENCE: 4
MASSTPSSSA TSSNAGADPN TTNLRPTTYD TWCGVAHGCT RKLGLKICGF LQRTNSLEEK    60
SRLVSAFKER QSSKNLLSCE NSDRDARFRR TETDFSNLFA RDLLPAKNGE EQTVQFLLEV    120
VDILLNYVRK TFDRSTKVLD FHHPHQLLEG MEGFNLELSD HPESLEQILV DCRDTLKYGV    180
RTGHPRFFNQ LSTGLDIIGL AGEWLTSTAN TNMFTYEIAP VFVLMEQITL KKMREIVGWS    240
SKDGDGIFSP GGAISNMYSI MAARYKYFPE VKTKGMAAVP KLVLFTSEQS HYSIKKAGAA    300
LGFGTDNVIL IKCNERGKII PADFEAKILE AKQKGYVPFY VNATAGTTVY GAFDPIQEIA    360
DICEKYNLWL HVDAAWGGGL LMSRKHRHKL NGIERANSVT WNPHKMMGVL LQCSAILVKE    420
KGILQGCNQM CAGYLFQPDK QYDVSYDTGD KAIQCGRHVD IFKFWLMWKA KGTVGFENQI    480
NKCLELAEYL YAKIKNREEF EMVFNGEPEH TNVCFWYIPQ SLRGVPDSPQ RREKLHKVAP    540
KIKALMMESG TTMVGYQPQG DKANFFRMVI SNPAATQSDI DFLIEEIERL GQDL          594

SEQ ID NO: 5              moltype = DNA   length = 1784
FEATURE                   Location/Qualifiers
source                    1..1784
                          mol_type = genomic DNA
                          organism = Homo sapiens
SEQUENCE: 5
atggcgtctc gacccccatct tcgtccgcaa cctcctcgaa cgcgggagcg gaccccaata    60
ccactaacct gcgccccaca acgtacgata cctggtgcgg cgtggcccat ggatgcacca    120
gaaaactggg gctcaagatc tgcggcttct tgcaaaggac caacagcctg gaagagaaga    180
gtcgccttgt gagtgccttc aaggagaggc aatcctccaa gaacctgctt cctgtgaaa     240
acagcgaccg ggatgcccgc ttccggcgca cagagactga cttctctaat ctgtttgcta    300
gagatctgct tccggctaag aacggtgagg agcaaaccgt gcaattcctc ctggaagtgg    360
tggacatact cctcaactat gtccgcaaga catttgatcg ctccaccaag gtgctggact    420
ttcatcaccc acaccagttg ctggaaggca tggagggctt caacttggag ctctctgacc    480
accccgagtc cctggagcag atcctggttg actgcagaga caccttgaag tatgggggttc    540
gcacaggtca tcctcgattt ttcaaccagc tctccactgg attggatatt attggcctag    600
ctggagaatg gctgacatca acggccaata ccaacatgtt tacatatgaa attgcaccag    660
tgtttgtcct catgaacaa  ataaacactta agaagatgag agatagagtt ggatggtcaa    720
gtaaagatgg tgatgggata ttttctcctg ggggcgccat atccaacatg tacagcatca    780
tggctgctcg ctacaagtac ttcccggaag ttaagacaaa gggcatggcg gctgtgccta    840
aactggtcct cttcacctca gaacagagtc actattccat aaagaaagct ggggctgcac    900
ttggctttgg aactgacaat gtgatttga taaagtgcaa tgaaaggggg aaaataattc    960
cagctgattt tgaggcaaaa attcttgaag ccaaacagaa gggatatgtt cccttttatg    1020
tcaatgcaac tgctggcacg actgtttatg gagcttttga tccgatacaa gagattgcag    1080
atatatgtga gaaatataac ctttggttgc atgtcgatgc tgcctgggga ggtgggctgc    1140
tcatgtccag gaagcaccgc cataaactca acggcataga aagggccaac tcagtcacct    1200
ggaaccctca caagatgatg ggcgtgctgt tgcagtgctc tgccattctc gtcaaggaaa    1260
agggtatact ccaaggatgc aaccagatgt gtgcaggata cctcttccag ccagacaagc    1320
agtatgatgt ctcctacgac accgggggaca aggcaattca gtgtggccgc cacgtggata    1380
tcttcaagtt ctggctgatg tggaaagcaa agggcacagt gggatttgaa aaccagatca    1440
acaaatgcct ggaactggct gaatacctct atgccaagat taaaaacaga gaagaatttg    1500
agatggtttt caatggcgag cctgagcaca caaacgtctg tttttggtat attccacaaa    1560
gcctcagggg tgtgccagac agccctcaac gacgggaaaa gctacacaag gtggctccaa    1620
aaatcaaagc cctgatgatg gagtcaggta cgaccatggt tggctaccag ccccaaggggg    1680
acaaggccaa cttcttccgg atggtcatct ccaacccagc cgctacccag tctgacattg    1740
acttcctcat tgaggagata gaaagactgg gccaggatct gtaa                    1784

SEQ ID NO: 6              moltype = AA   length = 178
FEATURE                   Location/Qualifiers
source                    1..178
                          mol_type = protein
                          organism = Rattus norvegicus
SEQUENCE: 6
MPGSALLCCL LLLAGVKTSK GHSIRGDNNC THFPVSQTHM LRELRAAFSQ VKTFFQKKDQ    60
LDNILLTDSL LQDFKGYLGC QALSEMIKFY LVEVMPQAEN HGPEIKEHLN SLGEKLKTLW    120
IQLRRCHRFL PCENKSKAVE QVKNDFNKLQ DKGVYKAMNE FDIFINCIEA YVTLKMKN     178

SEQ ID NO: 7              moltype = DNA   length = 682
FEATURE                   Location/Qualifiers
source                    1..682
                          mol_type = genomic DNA
                          organism = Rattus norvegicus
SEQUENCE: 7
catgcctggc tcagcactgc tatgttgcct gctcttactg gctggagtga agaccagcaa    60
aggccattcc atccggggtg acaataactg cacccacttc ccagtcagcc agacccacat    120
gctccgagag ctgagggctg ccttcagtca agtgaagact ttctttcaaa agaaggacca    180
```

```
gctggacaac atactgctga cagattcctt actgcaggac tttaagggtt acttgggttg    240
ccaagccttg tcagaaatga tcaagtttta cctggtagaa gtgatgcccc aggcagagaa    300
ccatggccca gaaatcaagg agcatttgaa ttccctggga gagaagctga agaccctctg    360
gatacagctg cgacgctgtc atcgatttct ccctgtgag  aataaaagca aggcagtgga    420
gcaggtgaag aatgatttta ataagctcca agacaaaggt gtctacaagg ccatgaatga    480
gtttgacatc ttcatcaact gcatagaagc ctacgtgaca ctcaaaatga aaaattgaac    540
cacccggcat ctactggact gcaggacata aatagagctt ctaaatctga tccagagatc    600
ttagctaacg ggagcaactc cttggaaaac ctcgtttgta cctctctcca aaatatttat    660
tacctctgat acctcagttc cc                                             682
```

```
SEQ ID NO: 8          moltype = DNA   length = 537
FEATURE               Location/Qualifiers
misc_feature          1..537
                      note = Optimized rat IL-10
source                1..537
                      mol_type = other DNA
                      organism = synthetic construct
SEQUENCE: 8
atgcctggct cagccctgct atgttgcctt ctcctgctgg cgggagtcaa gacaagcaag    60
ggccattcca tccgggggaga taataactgc acccacttcc cagtctctca aacccacatg   120
ttgcgagagc tgagggctgc cttcagtcag gtgaagacgt tcttccagaa gaaggaccag   180
ctggacaaca ttctgctgac tgacagcctg ctgcaggatt tcaagggtta tttggggtgt   240
caagccctgt ctgaaatgat caagttttac ctggtagaag tgatgcccca ggcagagaat   300
catggccccg agatcaagga gcacctcaac tccctggggg agaagctgaa gaccctgtgg   360
attcagctga ggcgctgcca cagatttctc ccctgtgaaa acaagagcaa ggcagtggag   420
caggtgaaga acgattttaa taagctccag gacaagggcg tctacaaggc catgaacgag   480
ttcgacatct ttatcaactg catagaagct tacgttacac tcaagatgaa gaattga      537
```

```
SEQ ID NO: 9          moltype = AA   length = 178
FEATURE               Location/Qualifiers
source                1..178
                      mol_type = protein
                      organism = Homo sapiens
SEQUENCE: 9
MHSSALLCCL VLLTGVRASP GQGTQSENSC THFPGNLPNM LRDLRDAFSR VKTFFQMKDQ    60
LDNLLLKESL LEDFKGYLGC QALSEMIQFY LEEVMPQAEN QDPDIKAHVN SLGENLKTLR   120
LRLRRCHRFL PCENKSKAVE QVKNAFNKLQ EKGIYKAMSE FDIFINYIEA YMTMKIRN     178
```

```
SEQ ID NO: 10         moltype = DNA   length = 1600
FEATURE               Location/Qualifiers
source                1..1600
                      mol_type = genomic DNA
                      organism = Homo sapiens
SEQUENCE: 10
aaaccacaag acagacttgc aaaagaaggc atgcacagct cagcactgct ctgttgcctg    60
gtcctcctga ctggggtgag ggccagccca ggccagggca cccagtctga aacagctgc   120
acccacttcc caggcaacct gcctaacatg cttcgagatc tccgagatgc cttcagcaga   180
gtgaagactt tctttcaaat gaaggatcag ctggacaact tgttgttaaa ggagtccttg   240
ctggaggact ttaagggtta cctgggttgc caagccttgt ctgagatgat ccagttttac   300
ctggaggagg tgatgcccca agctgagaac caagacccag acatcaaggc gcatgtgaac   360
tccctggggg agaacctgaa gaccctcagg ctgaggctca ggcgctgtca tcgatttctt   420
ccctgtgaaa acaagagcaa ggccgtggag caggtgaaga atgcctttaa taagctccaa   480
gagaaaggca tctacaaagc catgagtgag tttgacatct tcatcaacta catagaagcc   540
tacatgacaa tgaagatacg aaactgagac atcaggtgg  cgactctata gactctagga   600
cataaattag aggtctccaa aatcggatct ggggctctgg gatagctgac cagccccctt   660
gagaaacctt attgtacctc tcttataaa  tatttattac ctctgatacc tcaacccca   720
tttctattta tttactgagc ttctctgtga acgatttaga aagaagccca atattataat   780
tttttttcaat atttattatt ttcacctgtt tttaagctgt ttccataggg tgacacacta   840
tggtatttga gtgtttttaag ataaattata agttacataa gggaggaaaa aaaatgttct   900
ttggggagcc aacagaagct tccattccaa gcctgaccac gctttctagc tgttgagctg   960
ttttccctga cctccctcta atttatcttg tctctgggct tggggcttcc taactgctac   1020
aaatactctt aggaagagaa accagggagc ccctttgatg attaattcac cttccagtgt   1080
ctcggaggga ttcccctaac ctcattcccc aaccacttca ttcttgaaag ctgtggccag   1140
cttgttattt ataacaacct aaatttggtt ctaggccggg cgcggtggct cacgcctgta   1200
atcccagcac tttgggaggc tgaggcgggt ggatcacttg aggtcaggag ttcctaacca   1260
gcctggtcaa catggtgaaa ccccgtctct actaaaaata caaaaattag ccgggcatgg   1320
tggcgcgcac ctgtaatccc agctacttgg gaggctgagg caagagaatt gcttgaaccc   1380
aggagatgga agttgcagtg agctgatatc atgcccctgt actccagcct gggtgacaga   1440
gcaagactct gtctcaaaaa ataaaaataa aaataaattt ggttctaata gaactcagtt   1500
ttaactagaa tttattcaat tcctctggga atgttacatt gtttgtctgt cttcatagca   1560
gattttaatt ttgaataaat aaatgtatct tattcacatc                         1600
```

```
SEQ ID NO: 11         moltype = AA   length = 147
FEATURE               Location/Qualifiers
source                1..147
                      mol_type = protein
                      organism = Rattus norvegicus
SEQUENCE: 11
MGLSPHLAVT LFCFLICTGN GIHGCNDSPL REIINTLNQV TEKGTPCTEM FVPDVLTATR    60
```

-continued

```
NTTENELICR ASRVLRKFYF PRDVPPCLKN KSGVLGELRK LCRGVSGLNS LRSCTVNEST  120
LTTLKDFLES LKSILRGKYL QSCTSMS                                       147

SEQ ID NO: 12          moltype = DNA  length = 475
FEATURE                Location/Qualifiers
source                 1..475
                       mol_type = genomic DNA
                       organism = Rattus norvegicus
SEQUENCE: 12
tctcacgtca ctgactgtag agagctattg atgggtctca gcccccacct tgctgtcacc   60
ctgttctgct ttctcatatg taccgggaac ggtatccacg gatgtaacga cagccctctg  120
agagagatca tcaacacttt gaaccaggtc acagaaaaag ggactccatg caccgagatg  180
tttgtaccag acgtccttac ggcaacaagg aacaccacgg agaacgagct catctgcagg  240
gcttccaggg tgcttcgcaa attttacttc ccacgtgatg tacctccgtg cttgaagaac  300
aagtctgggg ttctcggtga actgaggaaa ctctgtagag gtgtcagcgg tctgaactca  360
ctgagaagct gcaccgtgaa tgagtccacg ctcacaacac tgaaagactt cctggaaagc  420
ctaaaaagca tcctacgagg gaaatacttg cagtcctgca cttccatgtc ctaac        475

SEQ ID NO: 13          moltype = DNA  length = 444
FEATURE                Location/Qualifiers
misc_feature           1..444
                       note = Optimized rat IL-4
source                 1..444
                       mol_type = other DNA
                       organism = synthetic construct
SEQUENCE: 13
atgggtttaa gcccccacct tgccgtcaca ctgttctgtt ttctcatctg taccgggaac   60
ggaattcatg gctgtaacga cagccctctg agagagatta tcaacacctt gaatcaggtt  120
accgaaaaag gcactccatg caccgagatg tttgtaccag atgtgcttac ggcaacgagg  180
aacaccactg agaatgagct gatctgtcgg gcttctcgga tgctgcgcaa attctacttc  240
cctcgtgatg tgccccgtg cttgaagaac aagtcaggcg tgctcggaga actgaggaag  300
ctctgcagag gcgtctcagg gctgaattct ctgcgcagct gcaccgtgaa tgaatccaca  360
ctcacaaccc tgaaagactt cctggagagc ctgaagagca tcctacgggg gaagtatctc  420
cagtcctgca cttccatgag ttga                                          444

SEQ ID NO: 14          moltype = AA  length = 153
FEATURE                Location/Qualifiers
source                 1..153
                       mol_type = protein
                       organism = Homo sapiens
SEQUENCE: 14
MGLTSQLLPP LFFLLACAGN FVHGHKCDIT LQEIIKTLNS LTEQKTLCTE LTVTDIFAAS   60
KNTTEKETFC RAATVLRQFY SHHEKDTRCL GATAQQFHRH KQLIRFLKRL DRNLWGLAGL  120
NSCPVKEANQ STLENFLERL KTIMREKYSK CSS                                153

SEQ ID NO: 15          moltype = DNA  length = 642
FEATURE                Location/Qualifiers
source                 1..642
                       mol_type = genomic DNA
                       organism = Homo sapiens
SEQUENCE: 15
tgcatcgtta gcttctcctg ataaactaat tgcctcacat tgtcactgca aatcgacacc   60
tattaatggg tctcacctcc caactgcttc cccctctgtt cttcctgcta gcatgtgccg  120
gcaactttgt ccacggacac aagtgcgata tcaccttaca ggagatcatc aaaactttga  180
acagcctcac agagcagaag actctgtgca ccgagttgac cgtaacagac atctttgctg  240
cctccaagaa cacaactgag aaggaaacct tctgcagggc tgcgactgtg ctccggcagt  300
tctacagcca ccatgagaag gacactcgct gcctgggtgc gactgcacag cagttccaca  360
ggcacaagca gctgatccga ttcctgaaac ggctcgacag gaacctctgg ggcctggcgg  420
gcttgaattc ctgtcctgtg aaggaagcca accagagtac gttggaaaac ttcttggaaa  480
ggctaaagac gatcatgaga gagaaatatt caaagtgttc gagctgaata ttttaattta  540
tgagtttttg atagctttat tttttaagta tttatatatt tataactcat cataaaataa  600
agtatatata gaatctaaaa aaaaaaaaaa aaaaaaaaa aa                       642

SEQ ID NO: 16          moltype = DNA  length = 28
FEATURE                Location/Qualifiers
misc_feature           1..28
                       note = Forward primer for amplifying CMV promoter
source                 1..28
                       mol_type = other DNA
                       organism = synthetic construct
SEQUENCE: 16
ttcggccgtc gaggagcttg gcccattg                                       28

SEQ ID NO: 17          moltype = DNA  length = 36
FEATURE                Location/Qualifiers
misc_feature           1..36
                       note = Reverse primer for amplifying CMV promoter
source                 1..36
                       mol_type = other DNA
```

-continued

```
                              organism = synthetic construct
SEQUENCE: 17
gacgtcgacc tagctagcga attcggggcc gcggag                            36

SEQ ID NO: 18          moltype = DNA  length = 34
FEATURE                Location/Qualifiers
misc_feature           1..34
                       note = Forward primer for amplifying SV40pA
source                 1..34
                       mol_type = other DNA
                       organism = synthetic construct
SEQUENCE: 18
ccatcgatca gacatgataa gatacattga tgag                              34

SEQ ID NO: 19          moltype = DNA  length = 43
FEATURE                Location/Qualifiers
misc_feature           1..43
                       note = Reverse primer for amplifying SV40pA
source                 1..43
                       mol_type = other DNA
                       organism = synthetic construct
SEQUENCE: 19
gacgtcgacg cggccgctac cacatttgta gaggtttttac ttg                   43

SEQ ID NO: 20          moltype = DNA  length = 28
FEATURE                Location/Qualifiers
misc_feature           1..28
                       note = Forward primer for amplifying Kanamycin resistant
                        gene
source                 1..28
                       mol_type = other DNA
                       organism = synthetic construct
SEQUENCE: 20
aggcgccatg agccatattc aacgggaa                                     28

SEQ ID NO: 21          moltype = DNA  length = 29
FEATURE                Location/Qualifiers
misc_feature           1..29
                       note = Reverse primer for amplifying Kanamycin resistant
                        gene
source                 1..29
                       mol_type = other DNA
                       organism = synthetic construct
SEQUENCE: 21
ttcatgatta gaaaaactca tcgagcatc                                    29

SEQ ID NO: 22          moltype = DNA  length = 28
FEATURE                Location/Qualifiers
misc_feature           1..28
                       note = Forward primer for amplifying LITR and CMV
source                 1..28
                       mol_type = other DNA
                       organism = synthetic construct
SEQUENCE: 22
atggcgcgcc cctggccttt tgctggcc                                     28

SEQ ID NO: 23          moltype = DNA  length = 28
FEATURE                Location/Qualifiers
misc_feature           1..28
                       note = Reverse primer for amplifying SV40pA and RITR
source                 1..28
                       mol_type = other DNA
                       organism = synthetic construct
SEQUENCE: 23
atggatccgc tagtaaatac cgcatcag                                     28

SEQ ID NO: 24          moltype = DNA  length = 20
FEATURE                Location/Qualifiers
misc_feature           1..20
                       note = Forward primer for amplifying rIL-10
source                 1..20
                       mol_type = other DNA
                       organism = synthetic construct
SEQUENCE: 24
ccgctagcgc caccatgcct                                              20
```

-continued

```
SEQ ID NO: 25        moltype = DNA  length = 39
FEATURE              Location/Qualifiers
misc_feature         1..39
                     note = Reverse primer for amplifying rIL-10
source               1..39
                     mol_type = other DNA
                     organism = synthetic construct
SEQUENCE: 25
gacgtcgacg ccatcgatgg cttaattaat caattcttc                        39
```

COMPOSITION FOR TREATING PAIN

CROSS REFERENCE TO RELATED APPLICATIONS

This application is a Continuation-in-Part of U.S. application Ser. No. 15/754,849 (allowed) filed Feb. 23, 2018, which is a National Stage of International Application No. PCT/KR2016/010480 filed Sep. 20, 2016, claiming priority based on Korean Patent Application No. 10-2015-0133349 filed Sep. 21, 2015.

SEQUENCE LISTING

The content of the electronically submitted sequence listing, file name: Sequence_Listing_As_Filed.txt; size: 32,606 bytes; and date of creation: Jul. 28, 2022, filed herewith, is incorporated herein by reference in its entirety.

TECHNICAL FIELD

The present invention relates to a composition for relieving or treating pain, the composition comprising a gene encoding glutamate decarboxylase (GAD) and a gene encoding an anti-inflammatory cytokine; and a method for relieving or treating pain by using the composition.

BACKGROUND ART

The term "pain" used by the International Association for the Study of Pain is defined as "actual or potential tissue damage or an unpleasant sensory and emotional experience associated therewith." Pain protects parts of the damaged body during the healing of the damage from the damage occurrence and motivates a human being to avoid similar experiences in the future. Most pain is relieved gradually if the cause of stimulus is removed, but sometimes the pain persists even though the damaged site has clearly healed as the stimulus has disappeared, or the pain develops in a state where no irritation, damage or disease has occurred.

Neuropathic pain is a type of non-malignant chronic pain that is induced by abnormality of a nerve, a spinal cord or a brain and is assumed that 1% or more of the population is suffering therefrom. The most common causes of neuropathic pain are trauma, metabolic and ischemic disorders, etc., which cause pathological nerve impulses to be transmitted to the brain through the spinal cord, resulting in pain occurrence. Neuropathic pain can be classified into peripheral neuropathic pain and central neuropathic pain depending on the location affected.

If such pain persists for a long period of time, it may lead to mental pain as well as physical pain, and thus, the life quality of a patient is likely to decline. Therefore, active treatment for pain relief should be carried out. Currently, as the pain itself is recognized as a disease and interests in pain is spreading, demand for analgesics is expected to increase steadily in the future. Mainly, analgesics such as acetylsalicylic acid, ibuprofen, and acetaminophen are widely used in current pain treatments. If aspirin, whose main ingredient is acetylsalicylic acid, is used for analgesic purposes, a high dose of at least 500 mg should be administered. However, since aspirin is a non-steroidal anti-inflammatory analgesic (NSAIDs) and interferes with the production of gastric mucosa by blocking the enzyme (COX-1) that promotes the production of prostaglandin which plays a role in protecting gastric mucosa, the stomach can be easily damaged by gastric acid and gastrointestinal bleeding can easily occur.

Further, since aspirin prevents thrombus formation, it can cause bleeding. Ibuprofen is also a non-steroidal anti-inflammatory analgesic ingredient, and therefore, it can cause gastric disturbances as well. In case of analgesics whose main ingredient is acetaminophen such as Tylenol, since acetaminophen is metabolized mostly in the liver, the liver may be damaged. Therefore, there are safety issues to lower its maximum dose, etc. In addition, long-term use of the above-mentioned analgesics often lead to resistance and loss of efficacies even if they are efficacious in the early stage, and specifically in case of chronic pain, there is a problem that the nonsteroidal anti-inflammatory agent is not effective even in the maximum dose for each patient, and thus high-dose administration for short term is prescribed. Therefore, the development of a new analgesic for pain which exhibits excellent analgesic efficacy at low dose without side effects is urgently required.

Currently, several new substances are being developed as analgesics for pain. Recently, sodium channel blockers have been developed, but they are mostly in the form of small molecules and have low selectivity to certain isoforms. Further, they show side effects such as cardio-toxicity, motor impairment, etc., and thus, more research in the future is necessary.

DISCLOSURE

Technical Problem

An example of the present invention relates to a composition for relieving or treating pain, which comprises a gene encoding GAD and a gene encoding an anti-inflammatory cytokine.

An additional example of the present invention is to provide a method for relieving or treating pain comprising administering a gene encoding GAD and a gene encoding an anti-inflammatory cytokine to a subject in need thereof.

Solution to Problem

The present invention provides a pharmaceutical composition for relieving or treating pain, which comprises a gene encoding GAD and a gene encoding an anti-inflammatory cytokine, and a method for relieving or treating pain comprising administering the same to a subject in need thereof.

Advantageous Effects

A pharmaceutical composition of the present invention can exhibit analgesic effect with only a small amount of gene delivery, and the pain-relieving efficacy can be observed even with a smaller amount of gene delivery as compared to single administration. Gamma-aminobutyric acid (GABA), a product of the GAD gene, has the efficacy of blocking pain signal transduction, but excessive amount of it can cause symptoms such as itching, dizziness, drowsiness, etc., as well as side effects such as increased heartbeat rate or respiration rate. Interleukin-10 (IL-10) is known to be a cytokine that exhibits anti-inflammatory effect, but side effects such as reducing red blood cell (RBC) level, etc., were observed when high dose was used systemically. On the other hand, a pharmaceutical composition of the present invention exhibits excellent analgesic efficacy even with a smaller dose by employing co-administration the combination of GAD and IL-10 as compared to single administration, and thus, it shows the synergistic efficacy of lowering conventional side effects and toxicity by low dose administration.

BRIEF DESCRIPTION OF DRAWINGS

FIG. 1 shows a vector map of the plasmid pAAV-hGAD65 used for the production of recombinant adeno-associated viruses.

FIG. 2 shows a vector map of the plasmid pAAV-rIL-10 used for the production of recombinant adeno-associated viruses.

FIG. 3 shows a vector map of the plasmid pAAV-rIL-4 used for the production of recombinant adeno-associated viruses.

FIG. 4 is a diagram confirming the expression level of each protein by Western blot, where adeno-associated viruses respectively introduced with GAD65, IL-10 and IL-4 genes were prepared, and then 293T cells, a human embryonic kidney cell line, were treated with the viruses, and cells or culture media were collected after 48 hours.

FIG. 5 illustrates the expression of GABA by a recombinant adeno-associated virus AAV-hGAD65, which is a diagram showing GABA levels in the media measured by ELISA, where 293T cells, a human embryonic kidney cell line, were treated with AAV-GAD65, and the culture media were collected after 48 hours. Two identical samples were prepared separately for each experiment group, and the bar represents the value for each sample.

FIG. 6 shows the results of comparing the efficacies of co-administration of AAV-GAD65 and AAV-IL-10 with gabapentin administration, which is a graph confirming the difference in synergistic efficacies of co-administration of AAV-GAD65 and AAV-IL-10 as compared to gabapentin used as a neuropathic pain reliever in the market.

FIG. 7 illustrates efficacies of AAV-GAD65 and AAV-IL-10 depending on combination composition ratios thereof. Particularly, it is a graph showing the synergistic effects in animal behavior analysis with the combination composition ratios of AAV-IL-10 to AAV-GAD of 1:1, 1:5, 1:30.

FIG. 8 is a graph showing the synergistic effects when AAV-GAD65 and AAV-IL-10 were co-administered at 1:10 and 1:30 by transforaminal epidural injection.

FIG. 9 shows the results of comparing the efficacies of AAV-GAD65 and AAV-IL-10 with AAV-GAD65 and AAV-IL-4, which illustrates the synergistic effects in animal behavior analysis when IL-10 and IL-4 were respectively combined with GAD65 for use.

FIG. 10 shows the expression of green fluorescent protein (GFP) in both the central and peripheral nervous systems by observing the GFP in both spinal cord and dorsal root ganglion (DRG) through intrathecal administration of AAV-GFP.

BEST MODE FOR CARRYING OUT EMBODIMENTS

Hereinafter, the present invention will be described in detail.

In one example of the present invention, a gene encoding GAD and a gene encoding an anti-inflammatory cytokine are provided in a form of being contained in a carrier, and the carrier includes viral vectors and non-viral vectors such as a plasmid, liposome, or the like.

The gene encoding GAD may be operably contained in a first vector, and the gene encoding an anti-inflammatory cytokine may be operably contained in a second vector.

The viral vector may be at least one selected from the group consisting of adenovirus, adeno-associated virus, herpes simplex virus, lentivirus, retrovirus and poxvirus.

A carrier containing a gene encoding GAD according to the present invention (e.g., a first vector) and a carrier containing a gene encoding an anti-inflammatory cytokine (e.g., a second vector) may have a virus titer-based mixing ratio per unit volume of 1:1 to 1:100, 1:1 to 1:80, 1:1 to 1:60, 1:1 to 1:40, 1:1 to 1:20, 1:1 to 1:10, 1:3 to 1:100, 1:3 to 1:80, 1:3 to 1:60, 1:3 to 1:40, 1:3 to 1:20, or 1:3 to 1:10, more preferably 1:1 to 1:50, and most preferably 1:5 to 1:30.

A pharmaceutical composition of the present invention can exhibit analgesic effect with only a small amount of genes or carriers containing the same. The composition of the present invention consists of a vector containing a gene encoding GAD and a vector containing an anti-inflammatory action gene in neural tissues, and the pain-relieving or treating efficacy can be achieved with a smaller amount as compared to single administration by co-administering substances having different analgesic mechanisms. Accordingly, since a composition of the present invention uses a small amount of genes or carriers containing the same, synergy of superior analgesic efficacies is shown while lowering toxicity.

In addition, the therapeutic effects of the present invention may be exerted regardless of the type of vector.

According to an example of the present invention, the first vector and the second vector may be adeno-associated viruses. The adeno-associated virus is not limited to a specific serotype, and preferably, it may be any one of AAV1 to AAV12, and AAVrh10.

GAD according to the present invention is an enzyme which decarboxylates glutamate to produce GABA. The gene encoding GAD applicable to the present invention may be one of GAD65 and GAD67, which are two isoforms. The GAD65 may be a human or rat protein or a gene encoding the same, and specific example thereof may consist of the amino acid sequence of SEQ ID NO: 1 of NCBI accession no. NM_000818, and also may consist of the base sequence of SEQ ID NO: 2 or SEQ ID NO: 3. The GAD67 may be a human or rat protein or a gene encoding the same, and specific example thereof may consist of the amino acid sequence of SEQ ID NO: 4 of NCBI accession no. NM_000817, and also may consist of the base sequence of SEQ ID NO: 5.

In a pharmaceutical composition according to the present invention, the inflammatory cytokine may be IL-10, and synergistic pain-relieving efficacy is exhibited by co-administration of IL-10 and GAD65.

The IL-10 is one of anti-inflammatory cytokines and is also known as a cytokine synthesis inhibitory factor (CSIF). IL-10 belongs to the class II cytokine and is a homodimer consisting of two subunits of 178 amino acids in length. IL-10 serves the function of inhibiting the activity of NK (natural killer) cells in an immune response, and is involved in signal transduction by forming a complex with the IL-10 receptor. IL-10 may be a human or rat protein or a gene encoding the same, and specific example thereof may consist of the amino acid sequence of SEQ ID NO: 6 of NCBI accession no. NM_012854 or SEQ ID NO: 9 of NCBI accession no. NM_000572, and also may consist of the base sequence of SEQ ID NO: 7, SEQ ID NO: 8 or SEQ ID NO: 10.

The base sequences of the gene encoding GAD and/or the gene encoding IL-10 of the present invention include mutants thereof, which may be base sequences modified by codon optimization for rats or humans. Specifically, the base sequences having sequence homology of at least 60%, preferably 70% or more, more preferably 80% or more, even more preferably 90% or more, most preferably 95% or more are included, where the "sequence homology %" is identified by comparing two optimally arranged sequences and comparison regions, and a part of the sequences in the comparison region may include addition or deletion (i.e., gap) as compared to a reference sequence (not including addition or deletion) regarding the optimal arrangements of the two sequences.

The present invention also provides a method for relieving and/or treating pain comprising administering a therapeutically effective amount of the pharmaceutical composition to a patient in need of relieving and/or treating pain. The above method may further comprise, prior to the administering step, determining the patient as a patient in need of relieving and/or treating pain. The term "therapeutically effective amount" may depend on the amount of an active gradient to achieve a desired efficacy, pain relief and/or therapeutic efficacy.

Further, the present invention relates to a method for relieving or treating pain in a subject with pain comprising administering a composition to the subject, wherein the composition comprises a vector comprising a gene encoding GAD and a gene encoding IL-10, and wherein the gene encoding GAD and the gene encoding IL-10 are operably linked to expression control sequences. In addition, the composition would comprise (a) a first vector comprising a gene encoding GAD; and (b) a second vector comprising a gene encoding IL-10, wherein the gene encoding GAD and the gene encoding IL-10 are operably linked to expression control sequences.

The pain according to the present invention may be nociceptive pain, neuropathic pain, psychogenic pain, mixed pain, inflammatory pain, visceral pain, or pathological pain. In addition, the pain may be osteoarthritis related pain, rheumatoid arthritis related pain, post-stroke pain, postoperative pain, multiple sclerosis related pain, trigeminal neuralgia, spinal cord injury related pain, phantom pain, idiopathic pain, post-herpetic neuralgia, diabetic neuropathic pain, HIV related pain, low back pain, cancer pain, fibromyalgia, internal organ pain, pancreatitis pain, migraine, or inflammatory bowel syndrome related pain.

Nociceptive pain is caused by primary lesions or nervous system dysfunction and evoked pain without the noxious stimulus. For example, nociceptive pain may be evoked by bruises, burns, cuts, fractures or broken bones, pain caused by repetitive or muscle overuse, or joint damages.

Neuropathic pain is caused by actual or potential tissues damage and generates pain signal with noxious stimulus. For example, neuropathic pain may be post-stroke pain, postoperative pain, migraine, HIV related pain, multiple sclerosis related pain, post-herpetic neuralgia, diabetic neuropathic pain, spinal cord injury related pain or trigeminal neuralgia etc.

Psychogenic pain is caused by beliefs, fears, or strong emotions, but the fundamental mechanism of pain is due to the abnormal nervous system.

Inflammatory pain is caused by various factors such as autoimmune disorders, toxins, and abnormal nervous system. For example, inflammatory pain may be osteoarthritis related pain, or rheumatoid arthritis related pain etc.

Visceral pain is generated due to swelling and stretching of internal organs, which can be caused by infection, trauma, cancer, direct damage, and abnormal signaling of visceral sensory fibers. For example, visceral pain may be a pancreatitis pain, or inflammatory bowel syndrome related pain etc.

Pathological pain (e.g., fibromyalgia etc.) is characterized by an amplified response to normal stimuli and characterized to has dysfunctional neuronal activity.

Mixed pain (e.g., low back pain, cancer pain etc.) is a complex overlap of different known pain types in any combination.

Preferably, a composition of the present invention may be used for relieving or treating neuropathic pain or chronic cancer pain. The term "relieving or treating" refers to any action that alleviates or improves pain symptom by administering a composition of the present invention.

An additional example of the present invention relates to a method for relieving or treating pain comprising administering a gene encoding GAD and a gene encoding an anti-inflammatory cytokine to a subject in need thereof. The subject may be a mammal including a human, or a cell and/or tissue isolated from a mammal including a human. Also, the subject may be a non-human animal, and the term "non-human animal" includes vertebrates such as mammals and non-mammals, for example, primates except humans, sheep, dogs, cats, horses, cows, chickens, amphibians, reptiles, etc.

There are various routes of administration for delivering genes to the nervous system using AAV. It is known that injection of AAV containing the GFP gene (AAV-GFP) into the thecal space expresses GFP protein in spinal cord and DRG, which represents central nervous system and peripheral nervous system, respectively (Andrew M Tan et al. doi: 10.2119/molmed.2015.00063) In addition, GFP protein is observed in both DRG and spinal cord even when AAV-GFP is injected into the vein or peritoneal, (Daniel J. Schuster et al. doi: 10.3389/fnana.2014.00042; Sandra Duque et al. doi:10.1038/mt.2009.71). Furthermore, therapeutic genes were delivered to the nervous system (i.e. central nervous system and peripheral nervous system) using direct DRG injection, transforaminal epidural injection, and intrathecal injection as performed in Examples 2 to 5. In other words, any kind of the route of administration in vivo does not affect the protein expression of therapeutic gene in both central and peripheral nervous systems. Therefore, analgesic effect of the present invention can be shown regardless of delivery route.

The therapeutically effective amount and administration route of a pharmaceutical composition of the present invention can be appropriately adjusted in consideration of a condition of the patient, a desired efficacy, and the like by those of ordinary skill in the art. For example, a composition according to the present invention may be provided in the form of an injection, and may include, for example, nerve injection, subcutaneous injection, intramuscular injection, or gene gun injection.

Mode for the Embodiments

Hereinafter, the present invention is explained in detail by Examples, but the following Examples are intended to further illustrate the present invention without limiting its scope.

<Example 1> Preparation and Property Analysis of Recombinant Adeno-Associated Viruses The adeno-associated viruses required for the present invention were prepared and produced based on the AAV helper-free system (Agilent, USA).

A. Preparation of pAAV-hGAD65

Figure 1:
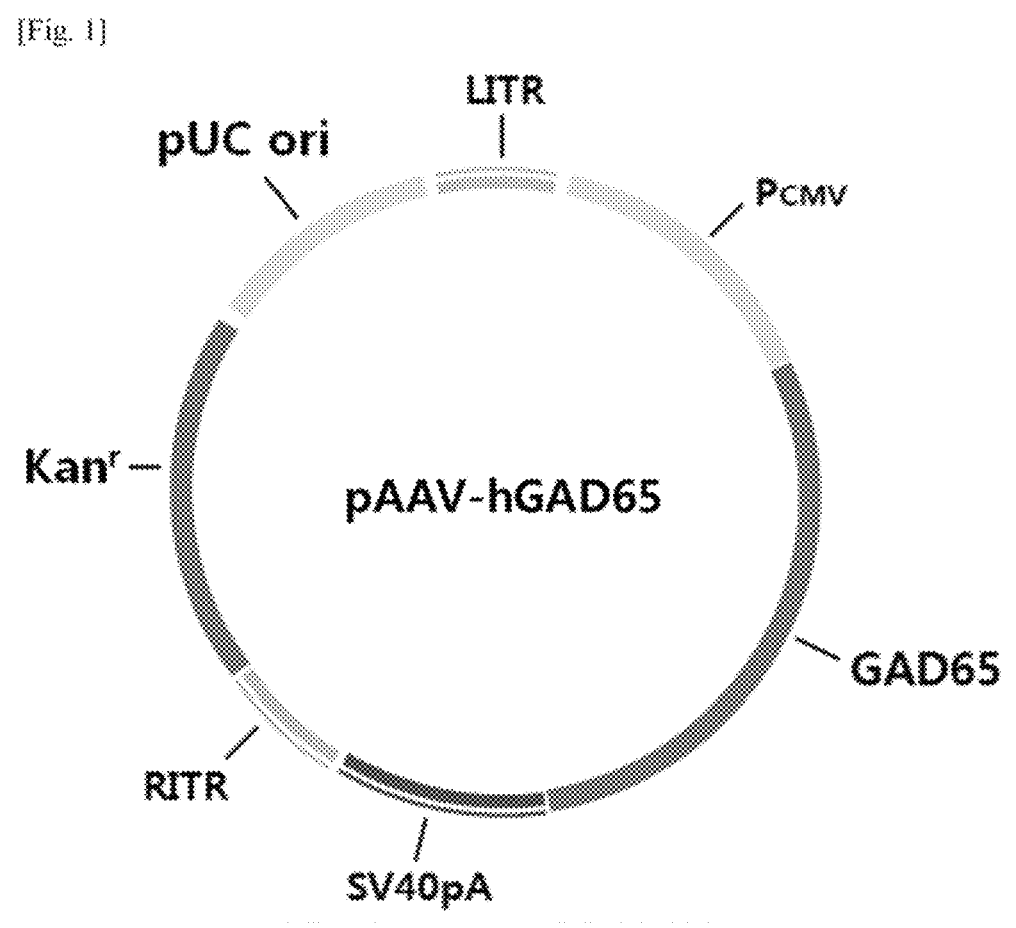

To prepare pAAV-hGAD65 of FIG. 1, the CMV promoter region of pJDK-rGAD65 [Lee B et al., Gene Ther, 12: 1215-1222 (2005)] was amplified by PCR and then introduced into pGEM-T (Promega, USA), to prepare pGEM-T-CMV. The primer sequences used for the amplification of CMV promoter are as follows.

```
F-JDK (SEQ ID NO: 16):
5'-TTCGGCCGTCGAGGAGCTTGGCCCATTG-3'

R-JDK (SEQ ID NO: 17):
5'-GACGTCGACCTAGCTAGCGAATTCGGGGCCGCGGAG-3'
```

The GAD65 gene was prepared by codon-optimization to fit for humans based on the human GAD65 sequence having the amino acid sequence of SEQ ID NO: 1 (NCBI NM_000818) and synthesizing the base sequence of SEQ ID NO: 3 (Bioneer, Korea). The hGAD65 gene introduced into pGEM-T was treated with NheI and SalI to obtain a 1.7 Kb DNA fragment, which was ligated to a 3.7 Kb DNA fragment obtained by treating pGEM-T-CMV with NheI and SalI, to complete pGEM-T-CMV-hGAD65.

SV40pA was amplified by performing PCR using pCI (Invitrogen, USA) as a template, followed by treatment with ClaI and SalI, to obtain a 222 bp DNA fragment. The above fragment was ligated to a 5.4 Kb DNA fragment prepared by cutting pGEM-T-CMV-hGAD65 with ClaI and SalI, to finally prepare pGEM-T-CMV-hGAD65-SV40pA. The primer sequences used for the amplification of SV40pA are as follows.

```
F-SV40pA (SEQ ID NO: 18):
5'-CCATCGATCAGACATGATAAGATACATTGATGAG-3'

R-SV40pA (SEQ ID NO: 19):
5'-GACGTCGACGCGGCCGCTACCACATTTGTAGAGGTTTTACTTG-3'
```

The ampicillin-resistance gene in pAAV-MCS (Agilent, USA) was replaced with kanamycin-resistance gene for the preparation of adeno-associated virus vectors. The kanamycin-resistance gene was amplified by PCR using pET-28(a) (Novagen, USA) as a template, and the amplified 816 bp kanamycin-resistance gene was ligated to pGEM-T, to prepare pGEM-T-Kan$^r$. The primer sequences used for the amplification of kanamycin-resistance gene are as follows.

```
F-Kan (SEQ ID NO: 20):
5'-AGGCGCCATGAGCCATATTCAACGGGAA-3'

R-Kan (SEQ ID NO: 21):
5'-TTCATGATTAGAAAAACTCATCGAGCATC-3'
```

For the introduction of the kanamycin-resistance gene, SpeI and EcoRV sites were respectively generated at the front and back of the ampicillin-resistance gene in pAAV-MCS by mutagenesis, and treated with SpeI and EcoRV, which was then ligated to the DNA fragment obtained by cutting the pGEM-T-Kan$^r$ prepared above with NheI and EcoRV, to prepare pAAV-MCS-Kan$^r$.

The prepared pAAV-MCS-Kan$^r$ was treated with NotI and BamHI, which was then ligated to a 2.7 Kb DNA fragment obtained by cutting pGEM-T-CMV-hGAD65-SV40pA with EagI and PvuI, to prepare pssAAV-GAD65.

In order to introduce the GAD65 expression cassette into pVAX1 (Invitrogen, USA), BamHI site was generated at the back of bGHpA by mutagenesis, which was then cut with MluI and NheI, to prepare DNA fragments. The LITR and CMV promoter regions were amplified by PCR using the pssAAV-GAD65 as a template, and cloned into pGEM-T easy (Promega, USA), which were then cut with AscI and NheI, and ligated to the pVAX1 vector prepared above, to prepare pVAX1-LITR-CMV. The primer sequences used for the amplification of LITR and CMV promoter regions are as follows.

```
F-ITR (SEQ ID NO: 22):
5'-ATGGCGCGCCCCTGGCCTTTTGCTGGCC-3'

R-JDK (SEQ ID NO: 17):
5'-GACGTCGACCTAGCTAGCGAATTCGGGGCCGCGGAG-3'
```

The pVAX1-LITR-CMV was prepared as a DNA fragment by cutting with NotI and NheI, and ligated to the DNA fragment prepared by cutting the pssAAV-GAD65 with EagI and NheI, to prepare pVAX1-LITR-CMV-hGAD65-SV40pA.

The pVAX1-LITR-CMV-hGAD65-SV40pA was cut with HpaI and BamHI, and then ligated to the DNA fragments obtained by treating the pGEM-T easy-SV40pA-RITR, which had been amplified by PCR using pssAAV-GAD65 as a template and cloned into pGEM-T easy, with HpaI and BamHI, to complete pVAX1-LITR-CMV-hGAD65-SV40pA-RITR (hereinafter, abbreviated as "pAAV-GAD65"). The primer sequences used for the amplification of SV40pA and RITR regions are as follows.

```
F-SV40pA (SEQ ID NO: 18):
5'-CCATCGATCAGACATGATAAGATACATTGATGAG-3'

R-ITR (SEQ ID NO: 23):
5'-ATGGATCCGCTAGTAAATACCGCATCAG-3'
```

The vector map of pAAV-hGAD65 is shown in FIG. 1.

B. Preparation of pAAV-rIL-10 pAAV-rIL-10 was prepared by a similar method to pAAV-hGAD65. Rat IL-10 gene was prepared by codon-optimization to fit for rats based on rat-derived base sequence (NCBI NM_012854) having the amino acid sequence of SEQ ID NO: 6 and synthesizing a gene having the base sequence of SEQ ID NO: 8 (Bioneer, Korea). The rIL-10 genes were amplified by PCR using the rat IL-10 genes introduced into pGEM-T easy as a template, and then treated with NheI and SalI to obtain a 0.5 Kb DNA fragment, which was then ligated to a 3.7 Kb DNA fragment obtained by cutting the pGEM-T-CMV with NheI and SalI, to prepare pGEM-T-CMV-rIL-10. The primer sequences used for the amplification of rIL10 is as follows.

```
F-rIL-10 (SEQ ID NO: 24):
5'-CCGCTAGCGCCACCATGCCT-3'

R-rIL-10 (SEQ ID NO: 25):
5'-GACGTCGACGCCATCGATGGCTTAATTAATCAATTCTTC-3'
```

SV40pA was amplified by performing PCR using pCI as a template, followed by treatment with NotI and SalI to obtain a 222 bp DNA fragment. The above fragment was ligated to a 4.2 Kb DNA fragment prepared by cutting pGEM-T-CMV-rIL-10 prepared above with ClaI and SalI, to prepare pGEM-T-CMV-rIL-10-SV40pA. The primer sequences used for the amplification of SV40pA are as follows.

F-SV40pA (SEQ ID NO: 18):
5'-CCATCGATCAGACATGATAAGATACATTGATGAG-3'

R-SV40pA (SEQ ID NO: 19):
5'-GACGTCGACGCGGCCGCTACCACATTTGTAGAGGTTTTACTTG-3'

Figure 2:
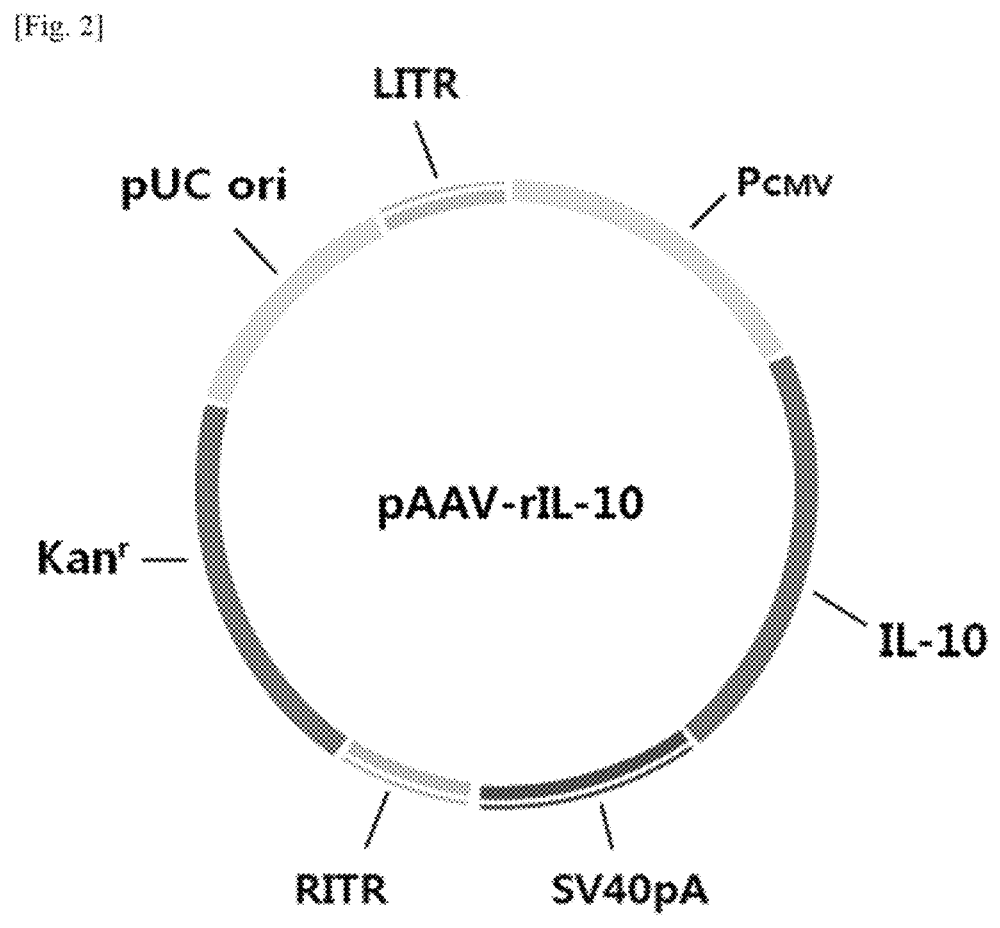

A 1.6 Kb DNA fragment was obtained by treating pGEM-T-CMV-rIL-10-SV40pA with EagI, and then ligated to the DNA fragment prepared by treating pAAV-MCS-Kan$^r$ with NoII and BamHI, to prepare pssAAV-CMV-rIL-10-SV40pA (hereinafter, abbreviated as "pAAV-rIL-10"). The vector map of pAAV-rIL-10 is shown in FIG. 2.

C. Preparation of pAAV-rIL-4

The rat IL-4 gene was prepared by codon-optimization to fit for rats based on the rat-derived base sequence (NCBI NM_201270) having the amino acid sequence of SEQ ID NO: 11 and synthesizing a gene having the base sequence of SEQ ID NO: 13 (Bioneer, Korea). The rIL-4 genes introduced into pGEM-B1 (Bioneer, Korea) were treated with NheI and NotI to obtain a 0.5 Kb DNA fragment. The above fragment was ligated to a 3 Kb DNA fragment prepared by treating pAAV-hGAD65 with NheI and NotI, to prepare pssAAV-CMV-rIL-4-SV40pA (hereinafter, abbreviated as "pAAV-rIL-4"). The vector map of pAAV-rIL-4 is shown in FIG. 3.

D. Property Analysis of Recombinant Adeno-Associated Viruses

The three types of plasmids (pAAV-hGAD65, pAAV-rIL-10 and pAAV-rIL-4) prepared above were respectively transfected into 293T cells, a human embryonic kidney cell line, with pHelper and pRC using PEI (Polysciences, USA). Herein, pRC5 into which the capsid gene of AAV serotype 5 was introduced was used for hGAD65, while pRC1 into which the capsid gene of AAV serotype 1 was introduced was used for rIL-10 and rIL-4. The transfected cells were cultured in a 37° C. incubator, collected after 48 hours, and subjected to 3 cycles of freezing and thawing to obtain each crude virus.

In order to confirm the protein expression of the recombinant adeno-associated viruses delivered to the cells, 293T cells, a human embryonic kidney cell line, were respectively treated with crude viruses AAV5-hGAD65, AAV1-rIL-10 and AAV1-rIL-4, the protein expression was confirmed by Western blot. Specifically, 8×10$^5$ 293 T cells were aliquoted into T25 flasks, and each flask was treated with 700 μL of crude viruses on the next day, followed by culturing in a 37° C. incubator. After 48 hours, the cells and the culture media were harvested separately, and the cells were dissolved with a solubilizing agent and the culture media were concentrated with amicon (Merck Millipore, Germany). The prepared samples were treated with the antibodies to GAD65 (Cell signaling, USA), IL-10 (Santa Cruz, USA) and IL-4 (Santa Cruz, USA), respectively, and subjected to Western blot. The results are shown in FIG. 4.

FIG. 4 is a diagram showing the expression of each protein by performing Western blot analysis of the cell lysates of 293T cell line, a human embryonic kidney cell line, treated with AAV5-hGAD65, AAV1-rIL-10 or AAV1-rIL-4. By confirming that a target protein was expressed in every case, it was confirmed that there was no problem in the structure and property of the recombinant adeno-associated viruses used in the experiment.

In order to confirm that GABA is produced by AAV5-hGAD65, the culture media of the cells treated with AAV5-GAD65 were collected under the same condition as that for sample preparation for Western blot, and subjected to GABA ELISA (LDN, Netherland) analysis. The results are shown in FIG. 5. Two identical samples were prepared separately for each experiment group, and the bar represents the value for each sample. As a result, it was confirmed that GABA was secreted into the culture medium by GAD65 introduced into the cells by AAV5-hGAD65 viruses.

E. Preparation of Recombinant Adeno-Associated Viruses

Recombinant adeno-associated viruses were prepared and purified by KRcrogen (Korea) for animal efficacy experiments, and the preparation method is as follows.

Three types of plasmids (pAAV-hGAD65, pAAV-rIL-10, and pAAV-rIL-4) prepared above were respectively transfected into 293T cells, a human embryonic kidney cell line, using calcium phosphate method with pHelper and pRC. Herein, pRC5 into which the capsid gene of AAV serotype 5 was introduced was used for hGAD65, while pRC1 into which the capsid gene of AAV serotype 1 was introduced was used for rIL-10 and rIL-4. The transfected cells were cultured in a 37° C. incubator, and collected after 48 hours.

Then, only the bands containing viruses were isolated and purified through high-speed centrifugation depending on cesium concentration gradient, to obtain AAV5-hGAD65, AAV1-rIL-10 and AAV1-rIL-4. The titers of the produced viruses were measured using qPCR method established by the manufacturer.

<Example 2> Analgesic Efficacy Test of AAV-IL-10 and AAV-GAD65 Via DRG Direct Injection A. Preparation of Administration Test Article 30 minutes before the animal administration, the recombinant adeno-associated virus stored at −80° C. were thawed at room temperature within 1 minute and mixed well by vortex. And Coomassie blue dye solution was prepared by mixing 10 mg of Coomassie blue in 1 mL of PBS well, and then filtering by syringe filters. 1 μL of AAV-GAD65 of 5.4×10$^5$ VG/μL, 1 μL of AAV-IL-10 of 1.8×10$^7$ VG/μL and 1 μL of 0.1% Coomassie blue dye were mixed under the calculation that each animal gets 3 μL in total. The test articles were prepared twice as much as the amount required, and 3 μL of the test article was administered to each animal.

As a control group, Gabapentin was mixed in animals' drinking water 1 hour prior to administration, which was prepared in a concentration of 10 mg/mL.

B. Preparation of Neuropathic Pain Animal Model and Test Article Administration

Male SD-rats of 180 to 200 g were anesthetized with inhalation anesthesia, and then upper parts of the calves were incised, and both ends of the common peroneal nerve and tibial nerve were tied and knots were made by 7-0 suture at 0.5-1 cm intervals. The regions of the two nerve bundles between the knots were cut by scissors and the incision site was sutured. Two weeks later, von Frey filament test was performed to confirm pain induction, and then the test substance was administered (C. J. Woolf, *Pain* 87, 2000).

The test substance was administered to DRG. After inhalation anesthesia of the pain animal model, rat's back at the lumbar (L) spine from L3 to L5 was linearly incised to expose vertebral bones, and then a transverse process, one of the spinal projections, was exposed at the side of the exposure, and the L4 process covering the DRG in the fixed state was carefully separated under the Stereo zoom microscopic view by a rongeur such that the DRG is not damaged. The area around the DRG was manipulated so that the DRG which extends in an oblique line was exposed like grains of rice.

A hamilton syringe was connected to a polyethylene catheter, and 3 µL of the test substance was accurately collected. Then, the syringe was replaced with a 1 mL syringe for the administration. The rats were placed on a small animal stereotaxic instrument, and the test article was injected while confirming that the micro-needle was pricking the L4 DRG accurately under a surgioscope. Herein, it was confirmed that the test article containing dye did not leak out of the DRG and was well delivered to the inside of the DRG. After confirming that entire test article was delivered to the DRG, the syringe was separated from the DRG, and suturing was done, and the animals were recovered.

Gabapentin was orally administered with 3 mg/kg.

C. Observation of Analgesic Efficacy Using Von Frey Filament Test

The 50% up & down threshold method established by Dixon in 1992 was employed since it is a commonly known method. The method calculates threshold values depending on a predetermined patterns of pain responses with a total of 8 filaments whose N values were 0.4, 0.6, 1, 2, 4, 6, 8 and 15 g, respectively. Pain occurrence regions were searched through changing positions from the region of most lateral toe to the heel of the sole where pain has occurred.

Rats abruptly lift the soles and shrink or lick the soles when pain occurs. Accordingly, when pain occurring region was found, the surrounding area was pricked 5 times with the filament of the next step and if there were responses for 3 times or more, it was regarded as a pain response, and the rats were observed with the filament of the next step. Patterns were recorded at every step. The pain patterns were recorded based on the pattern table established by S. R. Chaplan (Quantitative assessment of tactile allodynia in the rat paw. *Journal of Neuroscience Methods,* 1994) and the threshold values were calculated using it. The behavior analysis of the animal groups is performed by a blind method for 4 to 6 weeks, observed by at least 3 people, and the results of the recorded patterns are statistically processed to analyze the tendency of pain.

The results of pain-observation employing von Frey filament test where the pain animal model was administered with test articles are shown in FIG. 6. FIG. 6 shows the results of comparing the efficacies between co-administration of AAV-GAD65 and AAV-IL-10 and gabapentin administration. When GAD65 and IL-10 were co-administered, statistically significant pain-relieving effect was observed as compared to the untreated control group (negative control), and the effect was found to be higher than that of Gabapentin.

<Example 3> Analgesic Efficacy Tests of AAV-IL-10 and AAV-GAD65 Via the DRG Direct Injection A. Preparation of Administration Test Articles For the preparation of administration test articles, rAAV5-GAD65 and rAAV1-rIL-10 which were prepared in Example 1 and stored in a frozen state were thawed, and test articles were prepared in accordance with substantially the same method as the preparation method of administration test article in Example 2. Specifically, the single administration substance AAV-GAD65 or AAV-rIL-10 and the co-administration substances AAV-GAD65 and AAV-rIL-10 were diluted in PBS in a virus titer-based mixing ratio of 1:1, 1:5, or 1:30 as shown in Table 1, and 1 µL of 0.1% Coomassie blue dye was added to each test article under the calculation that each animal gets 3 µL. The test articles were prepared twice as much as the amount required for the total population, and 3 µL of the test article was administered to each animal.

TABLE 1

| Test articles | Virus types and contents | |
| --- | --- | --- |
| | AAV-GAD65 | AAV-IL-10 |
| Comparative Example 1 (GAD alone) | $5.4 \times 10^5$ VG/2 µL | — |
| Comparative Example 2 (IL-10 alone) | — | $1.8 \times 10^7$ VG/2 µL |
| Experimental Example 1 (1:1) | $5.4 \times 10^5$ VG/1 µL | $5.4 \times 10^5$ VG/1 µL |
| Experimental Example 2 (1:5) | $5.4 \times 10^5$ VG/1 µL | $2.7 \times 10^6$ VG/1 µL |
| Experimental Example 3 (1:30) | $5.4 \times 10^5$ VG/1 µL | $1.8 \times 10^7$ VG/1 µL |

B. Observation of Analgesic Efficacy Using Von Frey Filament Test

Test articles were administered to the pain animal models prepared by the same method as in Example 2, and pain was observed using a von Frey filament test, and the results are shown in FIG. 7.

FIG. 7 illustrates efficacies of AAV-GAD65 and AAV-IL-10 depending on composition ratios thereof. Particularly, compared to trace amounts of AAV-GAD65 and AAV-rIL-10 which showed no analgesic efficacy experiments with the mixing composition ratios of AAV-rIL-10 to AAV-GAD of 1:1 (Experimental Example 1), 1:5 (Experimental Example 2) and 1:30 (Experimental Example 3) exhibited synergistic efficacies in animal behavior analysis. As a result, the co-administration composition of AAV-GAD65 and AAV-rIL-10 according to the present invention showed an increasing pattern of the pain treatment efficacy as the mixing composition ratio of AAV-rIL-10 to AAV-GAD increased.

<Example 4> Analgesic Efficacy Tests of AAV-IL-10 and AAV-GAD65 Via Transforaminal Epidural Injection A. Preparation of Administration Test Articles 30 minutes before the animal administration experiment, the reagents kept at −80° C. were thawed at room temperature within 1 minute and mixed well by vortex. AAV-GAD65 and AAV-IL-10 were diluted in PBS to obtain the viral titers shown in Table 2. In order to administer 5 µL of the test article to each animal, the two virus diluted solutions were mixed half and half to obtain 1.5 times the volume required. Then, 5 µL of the test article was administered to each animal.

TABLE 2

| Test articles | Virus types and contents | |
| --- | --- | --- |
| | AAV-GAD65 | AAV-IL-10 |
| Experimental Example1 (1:10) | $5.0 \times 10^6$ VG/2.5 µL | $5.0 \times 10^7$ VG/2.5 µL |
| Experimental Example2 (1:30) | $5.0 \times 10^6$ VG/2.5 µL | $1.5 \times 10^8$ VG/2.5 µL |

B. Preparation of Neuropathic Pain Model and Test Article Administration

The neuropathic pain animal model was prepared by the same method as described in Example 2, and then the test article was administered.

The test article was administered by transforaminal epidural injection method at a position adjacent to the DRG. After inhalation anesthesia of the neuropathic pain animal model, rat's back at the lumbar spine from L3 to L5 was linearly incised to expose vertebral bones, and then, L4 transverse process, one of the spinal projections, was exposed at the side of the exposure. The rat was laid down sideways such that its side aspect could be seen from above, so that the L4 intervertebral foramen is visible.

A micro needle attached to the catheter was put into the prepared test article. A Hamilton syringe was connected to the opposite end of the catheter and pulled until reaching the marking of 5 μL to inject the test article into the catheter. After removing the Hamilton syringe from the catheter, the region at 1 cm from the tip of the needle was gripped by Halsted-Mosquito. As L4 spine was gripped by forceps and pulled upward, the tip area of the needle fixed by Halsted-Mosquito Straight was placed around the L4 intervertebral <Example 5> Comparison of Efficacies of AAV-GAD65 and AAV-IL-10 with AAV-GAD65 and AAV-IL-4 Via DRG Direct Injection A pain animal model was prepared by substantially the same method as in Example 2, and the preparation procedure of the administration test article was the same as well. AAV1-rIL-4 described in Example 1 was thawed and prepared for use in animal experiments as follows.

30 minutes before animal DRG administration experiment, the reagents stored at −80° C. were thawed at room temperature within 1 minute and mixed well by vortex. 10 mg of Coomassie blue was mixed well in 1 mL of PBS, and then, dyes filtered by syringe filters were prepared. AAV-GAD65 and AAV-rIL-4 were diluted in PBS to obtain the virus titer-based mixing ratios shown in Table 3, and 1 μL of 0.1% Coomassie blue dye was added to each test article under the calculation that each animal gets 3 μL. The test articles were prepared twice as much as the amount required for the total population, and 3 μL of the test article was administered to each animal.

TABLE 3

| Test articles | Virus types and contents | | |
| | AAV-GAD65 | AAV-IL-10 | AAV-IL-4 |
| --- | --- | --- | --- |
| Comparative Example 1 | $5.4 \times 10^5$ VG/2 μL | — | — |
| Comparative Example 2 | — | $1.8 \times 10^7$ VG/2 μL | — |
| Comparative Example 3 | — | — | $1.8 \times 10^7$ VG/2 μL |
| Comparative Example 4 | $5.4 \times 10^5$ VG/1 μL | — | $1.8 \times 10^7$ VG/1 μL |
| Experimental Example 1 | $5.4 \times 10^5$ VG/1 μL | $1.8 \times 10^7$ VG/1 μL | — | foramen. The tip of the needle was inserted into the intervertebral foramen whose space was secured, and advanced until the needle reached a bent portion inside the intervertebral foramen, and the needle which had been gripped was released. After confirming that the needle is fixed, a 1 mL syringe was connected to the polyethylene catheter connected to the opposite side of the needle. The piston was gently pressed to slowly administer the diluted administration substance to the rat DRG surrounding area, followed by suturing, to complete the administration procedure. By the same method as described in Example 2, pain results employing the von Frey filament test were observed at 4 weeks after administration of the substance. The results are shown in FIG. 8.

FIG. 8 shows that a mixture of AAV-GAD65 and AAV-IL-10 exhibits efficacy even when administered by the transforaminal epidural injection method. In addition, synergistic efficacy in animal behavior analysis was confirmed at the mixed composition ratio of AAV-GAD65 to AAV-IL-10 of 1:10 (Experimental Example 1) and 1:30 (Experimental Example 2).

The pain results employing the von Frey filament test were observed, and the results are shown in FIG. 9. The FIG. 9 shows the results of comparing the efficacies of AAV-GAD65 and AAV-rIL-10 with AAV-GAD65 and AAV-rIL-4, which illustrates the synergistic efficacies comparatively appearing in animal behavior analysis when IL-10 and IL-4, cytokines having anti-inflammatory effects, were used in combination with GAD65, respectively. As shown in FIG. 9, the pain treatment efficacy was insignificant or not observed when GAD65, IL-10 or IL-4 was administered alone, and no significant analgesic efficacy was observed when GAD65 and IL-4 were co-w administered as compared to the cases where GAD65 or IL-4 was administered alone. On the other hand, when GAD65 and IL-10 were co-administered, it was confirmed that there was higher analgesic efficacy which was statistically significant than the other comparative examples. In particular, synergistic pain-relieving effect was observed, which was not shown when GAD65 and IL-4 were co-administered.

<Example 6> Gene Delivery Via Intrathecal Administration

To see the GFP expression in the central and peripheral nervous system, AAV containing GFP gene was delivered to naïve rats via intrathecal injection. And it was confirmed that the GFP protein was expressed in both DRG and spinal cord, which represent peripheral nervous system and central nervous system, respectively.

A. Preparation of Test Article Administration 30 minutes before the animal administration experiment, the reagents kept at −80° C. were thawed at room temperature within 1 minute and mixed well by vortex. AAV-GFP was diluted in saline to obtain the accurate titers. In order to administer 5 μL of the test article to each animal, the two virus diluted solutions were mixed half and half to obtain 2 times the volume required. Then, 5 μL of the test article was administered to each animal.

B. Test Article Administration

The AAV-GFP manufactured by Nationwide children's hospital (NCH) was administered by intrathecal injection method. After inhalation anesthesia, animal's back at the lumbar spine from L4 to L5 was linearly incised to expose vertebral bones. A micro needle attached to the catheter was put into the prepared test article. A Hamilton syringe was connected to the opposite end of the catheter and pulled until reaching the marking of 5 μL to inject the test articles into the catheter. After removing the Hamilton syringe from the catheter, the region at 1 cm from the tip of the needle was gripped by Halsted-Mosquito. As L4 spine was gripped by forceps and pulled upward, the tip area of the needle fixed by Halsted-Mosquito Straight was placed around the L4-L5 interspinous ligament. The tip of the needle was inserted into the ligamentum flavum and advanced until the animal shows tail or hind paw flick behavior, and the needle and the L4 spine which had been gripped was released. After confirming that the needle is fixed, a 1 mL syringe was connected to the polyethylene catheter connected to the opposite side of the needle. The piston was gently pressed to slowly administer the administration substance to the rat intrathecal space, followed by suturing, to complete the administration procedure.

C. Observation of GFP Expression 3 weeks post administration, rats were anaesthetized and then transcardially perfused with followed by a 2% paraformaldehyde (PFA). DRG and spinal cord were isolated from rat and post-fixed in a 2% PFA solution overnight, followed by immersion in 15% and 30% sucrose solution for 48 h to achieve cryo-protection. Tissues mounted in O.C.T compound were sliced with a cryostat to obtain sections at 10 μm. The sections were incubated in 1M PBS for 5 min to remove O.C.T compound. Also, the sections were incubated in blocking solution (10% normal goat serum, 3% bovine serum albumin, 0.4% Triton X100, 1% glycine, 10% TBS in 1 M PBS) for 1 h, followed by anti-GFP antibody with blocking solution overnight at 4° C. After incubation with anti-GFP antibody, the sections were washed with 1M TBS for 5 min at 3 times in room temperature (RT) and incubated in Alexa Fluor 488-anti-chicken antibody with blocking solution for 1 h in RT. Again, the sections were incubated in 1M TBS for 5 min and then incubate with the 0.1 μg/μL DAPI solution for 5 min at RT. Finally, the sections were washed with 1M TBS for 5 min at 3 times in RT, and then mounted on silane 3 coated slide using fluorescence mounting medium. Fluorescence images were acquired by an axio scope A1 microscope.

3 weeks post AAV-GFP intrathecal administration, the GFP protein was observed in Cervical 1st (C1), Thoracic 5th (T5), Thoracic 13rd (T13), Lumbar 4th (L4), and L5 DRG (FIG. 10, upper). These results suggest that GFP gene is transfected and produce proteins in the peripheral nervous system when AAV-GFP is injected into the intrathecal space. Also, GFP protein was expressed in C1-2, T5-6, T13-L1 spinal cord (FIG. 10, below). That is to say that the GFP gene delivered and synthesized proteins in the central nervous system when AAV-GFP is administrated intrathecally. Taken together, therapeutic genes can deliver not only into the peripheral nervous system but also central nervous system via intrathecal injection.

Other study group showed that the gene expressed in both DRG and spinal cord through the various gene delivery route, not only intrathecal injection but also systemic administration such as intravenous injection and subcutaneous injection. Combining with the results, AAV containing any genes can express in both central and peripheral nervous systems without limitation to the route of administration.

The invention claimed is:

1. A method for relieving or treating pain in a subject with pain comprising administering a composition to the subject, wherein the composition comprises a vector comprising a gene encoding glutamate decarboxylase (GAD) and a gene encoding interleukin-10 (IL-10), and wherein the gene encoding GAD and the gene encoding IL-10 are operably linked to expression control sequences.

2. The method of claim 1, wherein the vector comprises (a) a first vector comprising the gene encoding GAD; and (b) a second vector comprising the gene encoding IL-10.

3. The method of claim 1, wherein the vector is a viral vector selected from the group consisting of adenovirus, adeno-associated virus (AAV), herpes simplex virus, lentivirus, retrovirus, and poxvirus.

4. The method of claim 2, wherein a ratio of vector genomes (VG) of the first vector per μl of the composition and vector genomes (VG) of the second vector per μl of the composition is 1:1 to 1:50.

5. The method of claim 1, wherein the GAD is one or more selected from the group consisting of GAD65 and GAD67.

6. The method of claim 1, wherein the GAD consists of the amino acid sequence of SEQ ID NO: 1 or SEQ ID NO: 4.

7. The method of claim 1, wherein the gene encoding GAD consists of the nucleotide sequence of SEQ ID NO: 2, SEQ ID NO: 3 or SEQ ID NO: 5.

8. The method of claim 1, wherein the IL-10 consists of the amino acid sequence of SEQ ID NO: 6 or SEQ ID NO: 9.

9. The method of claim 1, wherein the gene encoding IL-10 consists of the nucleotide sequence of SEQ ID NO: 7, SEQ ID NO: 8 or SEQ ID NO: 10.

10. The method of claim 1, wherein the pain is nociceptive pain, neuropathic pain, psychogenic pain, mixed pain, inflammatory pain, visceral pain, or pathological pain.

11. The method of claim 10, wherein the pain is osteoarthritis related pain, rheumatoid arthritis related pain, post-stroke pain, postoperative pain, multiple sclerosis related pain, trigeminal neuralgia, spinal cord injury related pain, phantom pain, idiopathic pain, post-herpetic neuralgia, diabetic neuropathic pain, HIV related pain, low back pain, cancer pain, fibromyalgia, internal organ pain, pancreatitis pain, migraine, or inflammatory bowel syndrome related pain.

12. The method of claim 1, wherein the composition further comprises a physiologically acceptable carrier.

13. The method of claim 1, wherein the composition is suitable for an injection.

* * * * *